United States Patent
Miklatzky et al.

(10) Patent No.: US 10,012,588 B2
(45) Date of Patent: Jul. 3, 2018

(54) APPARATUS AND METHOD FOR CUSTOMIZED HAIR-COLORING

(71) Applicant: COLORIGHT LTD., Rehovot (IL)

(72) Inventors: Efraim Miklatzky, Neve Ilan (IL); Elena Ishkov, Givataim (IL); Daniel Mandelik, Rehovot (IL); Gilad Davara, Rehovot (IL)

(73) Assignee: COLORIGHT LTD., Rehovot (IL)

( * ) Notice: Subject to any disclaimer, the term of this patent is extended or adjusted under 35 U.S.C. 154(b) by 0 days.

(21) Appl. No.: 15/303,726

(22) PCT Filed: Apr. 27, 2015

(86) PCT No.: PCT/IB2015/053065
§ 371 (c)(1),
(2) Date: Oct. 12, 2016

(87) PCT Pub. No.: WO2015/166403
PCT Pub. Date: Nov. 5, 2015

(65) Prior Publication Data
US 2017/0038297 A1    Feb. 9, 2017

Related U.S. Application Data

(60) Provisional application No. 61/984,796, filed on Apr. 27, 2014.

(51) Int. Cl.
*G01J 1/10* (2006.01)
*G01N 21/47* (2006.01)
(Continued)

(52) U.S. Cl.
CPC .......... *G01N 21/47* (2013.01); *A45D 44/005* (2013.01); *G01J 3/463* (2013.01); *G01N 21/25* (2013.01);
(Continued)

(58) Field of Classification Search
CPC .... G01J 3/463; G01J 3/50; G01J 3/524; G01J 2003/466; G01J 3/02; G01J 3/462;
(Continued)

(56) References Cited

U.S. PATENT DOCUMENTS 4,643,313 A    2/1987 Robson
5,205,837 A    4/1993 Andrean et al.
(Continued)

FOREIGN PATENT DOCUMENTS

CA    2828363 A1    3/2015
DE    3609962 A1    6/1987
(Continued)

OTHER PUBLICATIONS

Birngruber C et al: The color(s) of human hair-Forensic hair analysis with SpectraCube; vol. 185, No. 1-3, Mar. 10, 2009, pp. e19-e23; Forensic Science International, Elsevier Scientific Publishers Ireland LTD, IE; available online Jan. 24, 2009.
(Continued)

*Primary Examiner* — Michael P Stafira
(74) *Attorney, Agent, or Firm* — Oblon, McClelland, Maier & Neustadt, L.L.P.

(57) ABSTRACT

An apparatus and method for customized hair-coloring is disclosed. In some embodiments the method comprises: a. performing a plurality of light-scattering measurements upon a sample of hair such that for each light-scattering measurement, the sample of hair is illuminated from a different respective direction; b. comparing the results of the light-scattering measurements; c. in accordance with results of the comparing, computing an initial damage-state of hair of the sample by comparing the results of the light-scattering measurements; d. obtaining an initial color-state of the hair of the sample; and e. computing a hair-coloring composition that is predicted to transform the hair sample from the initial
(Continued)

color-state to a target color-state such that in response to a determining of a greater (lesser) extent of initial damage, a concentration of artificial-colorant(s) within the computed coloring composition is reduced (increased).

23 Claims, 17 Drawing Sheets

(51) Int. Cl.
  *G01J 3/46* (2006.01)
  *G01N 21/25* (2006.01)
  *G01N 21/55* (2014.01)
  *A45D 44/00* (2006.01)
  *G01N 33/483* (2006.01)
(52) U.S. Cl.
  CPC ......... *G01N 21/4738* (2013.01); *G01N 21/55* (2013.01); *G01N 33/4833* (2013.01); *A45D 2044/007* (2013.01); *G01N 2021/4711* (2013.01); *G01N 2021/4735* (2013.01); *G01N 2201/12* (2013.01)
(58) Field of Classification Search
  CPC .. G01J 3/465; G01J 3/0208; G01J 3/46; G01J 3/0291; G01J 3/06; G01J 3/52; G01J 3/0264; G01J 3/18; G01J 3/0251
  See application file for complete search history.

(56) References Cited

U.S. PATENT DOCUMENTS

| | | |
|---|---|---|
| 5,660,342 A | 8/1997 | Bock |
| 5,754,283 A | 5/1998 | Keane et al. |
| 5,851,181 A | 12/1998 | Talmor |
| 5,990,058 A | 11/1999 | Bac et al. |
| 6,096,359 A | 8/2000 | Bombardelli et al. |
| 6,170,980 B1 | 1/2001 | Martin |
| 6,248,749 B1 | 6/2001 | Demarchez et al. |
| 6,330,341 B1 | 12/2001 | MacFarlane et al. |
| 6,362,885 B1 | 3/2002 | Osumi et al. |
| 6,529,446 B1 | 3/2003 | De La Huerga |
| 6,547,833 B2 | 4/2003 | Casperson et al. |
| 6,613,311 B2 | 9/2003 | Imperial |
| 6,707,929 B2 | 3/2004 | Marapane et al. |
| 6,764,523 B2 | 7/2004 | Casperson et al. |
| 6,790,240 B2 | 9/2004 | Schulze zur Wiesche et al. |
| 6,807,297 B1 | 10/2004 | Tankovich et al. |
| 6,818,022 B2 | 11/2004 | Massoni |
| 6,984,377 B2 | 1/2006 | Withiam et al. |
| 7,110,117 B2 | 9/2006 | Grossinger et al. |
| 7,204,856 B2 | 4/2007 | Schulze Zur Wiesche et al. |
| 7,304,739 B2 | 12/2007 | Grossinger et al. |
| 7,458,992 B2 | 12/2008 | Schmenger et al. |
| 7,463,356 B2 | 12/2008 | Grossinger et al. |
| 7,508,508 B2 | 3/2009 | Grossinger et al. |
| 7,523,018 B2 | 4/2009 | Grossinger et al. |
| 7,708,021 B2 | 5/2010 | Ghannad et al. |
| 2001/0002025 A1 | 5/2001 | Rolf-Dieter et al. |
| 2002/0010556 A1 | 1/2002 | Marapane et al. |
| 2002/0157191 A1 | 10/2002 | Casperson et al. |
| 2002/0194684 A1 | 12/2002 | Wiesche et al. |
| 2003/0028978 A1 | 2/2003 | Schulze Zur Wiesche et al. |
| 2004/0000015 A1 | 1/2004 | Grossinger et al. |
| 2004/0013616 A1 | 1/2004 | Withiam et al. |
| 2005/0015895 A1 | 1/2005 | Azizova et al. |
| 2005/0019398 A1 | 1/2005 | Kotharl et al. |
| 2005/0036677 A1 | 2/2005 | Ladjevardi |
| 2005/0039271 A1 | 2/2005 | Schulze Zur Wiesche et al. |
| 2005/0165705 A1 | 7/2005 | Lauper et al. |
| 2005/0177032 A1 | 8/2005 | Grossinger et al. |
| 2005/0244343 A1 | 11/2005 | Withiam et al. |
| 2006/0149151 A1 | 7/2006 | Ladjevardi et al. |
| 2006/0195300 A1 | 8/2006 | Grossinger et al. |
| 2007/0159290 A1 | 7/2007 | Grossinger et al. |
| 2007/0265867 A1 | 11/2007 | Lin |
| 2008/0013077 A1 | 1/2008 | Orelli et al. |
| 2008/0068604 A1 | 3/2008 | Grossinger et al. |
| 2008/0256724 A1 | 10/2008 | Bolton et al. |
| 2009/0119852 A1 | 5/2009 | Marsh |
| 2011/0038818 A1 | 2/2011 | Onyebuagu et al. |
| 2012/0320191 A1 | 12/2012 | Meschkat et al. |
| 2014/0082854 A1* | 3/2014 | Landa ............... A45D 19/02 8/405 |

FOREIGN PATENT DOCUMENTS

| | | |
|---|---|---|
| DE | 4205112 A1 | 8/1993 |
| DE | 10260880 A1 | 7/2004 |
| DE | 102006008149 A1 | 8/2007 |
| EP | 0590538 A1 | 4/1994 |
| EP | 1817976 A1 | 8/2007 |
| EP | 2081668 A1 | 7/2009 |
| EP | 2133673 A1 | 12/2009 |
| EP | 2193781 A1 | 6/2010 |
| FR | 2402446 A1 | 4/1979 |
| FR | 2532174 A1 | 3/1984 |
| FR | 2901131 A1 | 11/2007 |
| JP | 2000116622 A | 4/2000 |
| JP | 2004198398 A | 7/2004 |
| JP | 2004212088 A | 7/2004 |
| JP | 2007212140 A | 8/2007 |
| JP | 2008285429 A | 11/2008 |
| KR | 100802645 A | 9/2004 |
| KR | 20040076861 A | 9/2004 |
| KR | 10-2014-0027952 | 3/2014 |
| WO | 0145647 A2 | 6/2001 |
| WO | 02083282 A1 | 10/2002 |
| WO | 03012728 A1 | 2/2003 |
| WO | 03074015 A1 | 9/2003 |
| WO | 2004058202 A1 | 7/2004 |
| WO | 2004082650 A1 | 9/2004 |
| WO | 2004101689 A2 | 11/2004 |
| WO | 2008046518 A1 | 4/2008 |
| WO | 2009121643 A2 | 10/2009 |
| WO | 2009152033 A1 | 12/2009 |
| WO | 2010004565 A2 | 1/2010 |
| WO | 2010060601 A1 | 6/2010 |
| WO | 2010100231 A1 | 9/2010 |
| WO | 11003554 A2 | 1/2011 |
| WO | 2012032671 A1 | 3/2012 |
| WO | 2012127429 A1 | 9/2012 |

OTHER PUBLICATIONS

WO 2008046518 Machine Translation (by EPO and Google); published on Apr. 24, 2008 Beiersdorf AG et al.
DE 10260880 Machine Translation (by EPO and Google); published on Jul. 1, 2004, Henkel KGAA.
DE 3609962 Machine Translation (by EPO and Google); published on Jun. 19, 1987, Panke Hartmut.
DE 4205112 Machine Translation (by EPO and Google); published on Aug. 26, 1993, Brackmann Hans Peter Dr Med.
EP 2081668 Machine Translation (by EPO and Google); published on Jul. 29, 2009, Beiersdorf AG.
WO 2009121643 Machine Translation (by EPO and Google); published on Oct. 8, 2009, Henkel AG & Co KGAA et al.
FR 2402446 Machine Translation (by EPO and Google); published on Apr. 6, 1979, Oreal.
FR 2532174 Machine Translation (by EPO and Google); published on Mar. 2, 1984, Bristol Myers Co.
FR 2901131 Machine Translation (by EPO and Google); published on Nov. 23, 2007, Oreal.
International Search Report for PCT/IB2015/000724; search report dated Nov. 16, 2015.
International Search Report for PCT/IB2015/053065; search report dated Sep. 1, 2015.
International Search Report for PCT/IL2014/50850; search report dated Mar. 23, 2015.

(56) References Cited

OTHER PUBLICATIONS

JP 2000116622 Machine Translation (by EPO and Google); published on Apr. 25, 2000, Kose Corp.
JP 2004198398 Machine Translation (by EPO and Google); published on Jul. 15, 2004, Kose Corp.
JP 2004212088 Machine Translation (by EPO and Google); published on Jul. 29, 2004, Kose Corp.
JP 2007212140 Machine Translation (by EPO and Google); published on Aug. 23, 2007, Kose Corp.
JP 2008285429 Machine Translation (by EPO and Google); published on Nov. 27, 2008, Shiseido Co Ltd.
KR100802645 Machine Translation (by EPO and Google); published on Sep. 3, 2004.
KR20040076861 Machine Translation (by EPO and Google); published on Sep. 3, 2004.
WO 0145647 Machine Translation (by EPO and Google); published on Jun. 28, 2001, Henkel Kgaa et al.
WO 03074015 Machine Translation (by EPO and Google); published on Sep. 12, 2003, Henkel Kgaa et al.
WO 2004082650 Machine Translation (by EPO and Google); published on Sep. 3, 2004, Henkel Kgaa et al.
Written Opinion for PCT/IB2015/000724; written opinion dated Nov. 16, 2015.
Written Opinion for PCT/IB2015/053065; written opinion dated Sep. 1, 2015.
Written Opinion for PCT/IL2014/50850; written opinion dated Mar. 23, 2015.
DE 102006008149 Machine Translation (by EPO and Google); published on Aug. 23, 2007, Henkel Kgaa.
Office Action dated Dec. 10, 2017 in Korean Patent Application No. 10-2016-7031806 with English translation, 8 pages.

\* cited by examiner

APPARATUS AND METHOD FOR CUSTOMIZED HAIR-COLORING

CROSS-REFERENCE TO RELATED APPLICATIONS

The present application claims priority to U.S. application Ser. No. 61/984,796 filed on Apr. 27, 2014, which is incorporated herein by reference in its entirety.

FIELD OF THE DISCLOSURE

The present disclosure relates to coloring of keratinous fibers, more specifically to customized hair-coloring.

BACKGROUND

Hair-coloring has been practiced for millennia, and continues to play an important role in modern society. A central problem in the art of hair-coloring is to provide the correct treatment—e.g. the appropriate hair-coloring composition and/or treatment parameters (e.g. treatment time, temperature, etc).

For the present disclosure, a lair-coloring treatment is any treatment which modifies the color of hair shafts. Examples of hair-coloring treatments include hair-dying treatments (e.g. based upon artificial colorants) and bleaching. Hair-dying treatments include temporary, demi-permanent, semi-permanent or permanent hair-dying (e.g. oxidative hair-dying) treatments.

In recent years, computer-based techniques have been developed where a user provides a hair-coloring target (e.g. an LAB value), data describing the user's 'initial hair' (i.e. before the hair-coloring treatment) is stored in computer memory, and a customized hair-coloring composition specific for the user's hair is computed. For example, the data describing a color-state of 'initial hair' may be measured using an optical device such as a spectrometer or a colorimeter or a camera—this data may include an initial pre-treatment LAB value or an initial pre-treatment spectrum (e.g. reflection-spectrum) of the hair. Once this data is obtained, a number of hypothetical post-treatment hair treatments are analyzed, and a respective predicted post-treatment color state (e.g. LAB value or spectrum of the hair) is computed for each hypothetical hair-treatments.

The hypothetical hair-coloring treatments may then be scored based upon a 'color difference' (e.g. a distance in LAB space) between (i) the predicted post-treatment color state of the hair for each treatment and (ii) the hair-coloring target (e.g. a distance in LAB space. According to the scores, a preferred hair-coloring treatment is selected from the hypothetical or 'candidate' hair-coloring treatments.

In particular, the hair-coloring treatment having the minimum 'color difference' may be selected as the 'best-matching' hair-coloring treatment. The preferred hair-coloring treatment typically requires application (and hence manufacture) of one or more hair-coloring composition—each composition may be specified by quantities or concentrations of ingredients (e.g. dyes, base, coupler, lifting agent) therein.

The ingredients for manufacture of the customized hair-coloring composition may be provided by automatically dispensing the requisite ingredients from a dispenser device that is operatively linked to electronic circuitry configured to compute the hair-coloring treatment that is predicted to transform the hair from its initial color state to the target state. It is appreciated that the quality of the hair-coloring composition (i.e. its ability to indeed transform the user's physical hair to the desired color-state) is depends upon how accurately a final post-hair-coloring-treatment color state is predicted.

To date, there is an ongoing need for apparatus and methods of ascertaining a current status of a user's hair—e.g. for the purpose of accurately dispensing the correct combination of ingredients for a hair-coloring composition.

SUMMARY

A hair coloring method comprises: a. performing a plurality of light-scattering measurements upon a sample of hair such that for each light-scattering measurement, the sample of hair is illuminated from a different respective direction; b. comparing the results of the light-scattering measurements; c. in accordance with results of the comparing, computing an initial damage-state of hair of the sample by comparing the results of the light-scattering measurements; d. obtaining an initial color-state of the hair of the sample; and e. computing a hair-coloring composition that is predicted to transform the hair sample from the initial color-state to a target color-state such that in response to a determining of a greater (lesser) extent of initial damage, a concentration of artificial-colorant(s) within the computed coloring composition is reduced (increased)—i.e. in response to a determining of a greater extent of initial damage, a concentration of artificial-colorant(s) within the computed coloring composition is reduced and/or in response to a determining of a lesser extent of initial damage, a concentration of artificial-colorant(s) within the computed coloring composition is increased.

In some embodiments, i. the hair-coloring composition comprises first and second artificial-colorants ii. the rate of absorbance by hair-shafts of the first artificial-colorant exhibits a greater dependency upon an extent of damage to the hair-shafts than the rate of absorbance of hair-shafts of the second artificial-colorant; iii. in response to a determining of a greater extent of initial damage, a ratio between respective concentrations of the first and second artificial-colorants within the hair-coloring composition decreases.

A method of coloring hair according to (i) a preferred target color-state and (ii) a maximum hair-damage-threshold comprises: a. obtaining descriptions of an initial damage state of the hair and an initial color-state of the hair; and b. according to the initial damage-state of the hair, determining an availability of a damage-threshold-compliant hair-coloring treatment that is predicted to (i) successfully transform the color-state of the hair from the initial color-state to the preferred target color-state; and (ii) is predicted to maintain a damage-state of the hair below the maximum-damage-threshold; and c. in response to a determination that the damage-threshold-compliant hair-treatment is not available, performing at least one of the following: (i) presenting to a user one or more alternate target color-states where each alternate target color-state: A. deviates from the preferred target color-state; and B. is associated with a damage-threshold-compliant hypothetical hair-treatment that is predicted to transform the color-state of the hair from the initial color-state to the alternate target color-state: I. without exceeding the damage-threshold; and II. in a manner that minimizes a color-difference between the alternate color-state and the preferred target color-state; (ii) presenting to a user a description of one or more of the damage-threshold-compliant hypothetical treatments; (iii) dispensing ingredients for a hair-coloring composition required by the damage-threshold-compliant hypothetical treatment; and (iv) generating an alert signal.

A hair coloring method comprises: a. performing a plurality of light-scattering measurements upon a sample of hair such that for each light-scattering measurement, the sample of hair is illuminated from a different respective direction; b. electronically comparing the results of the light-scattering measurements; c. in accordance with results of the comparing, computing an initial damage-state of hair of the sample by comparing the results of the light-scattering measurements; d. obtaining an initial color-state of the hair of the sample; and e. computing a hair-coloring composition that is predicted to transform the hair sample from the initial color-state to a target color-state such that: (i) in response to a determining of a greater (lesser) extent of initial damage, a concentration of artificial-colorants within the computed coloring composition is reduced (increased); and/or (ii) in response to a determining of a greater (lesser) extent of initial damage, a lifting intensity of the hair-coloring composition is reduced (increased); and/or (iii) in response to a determining of a greater (lesser) extent of initial damage, a concentration of alkalizing agents (e.g. ammonia) in the hair-coloring composition is reduced (increased).

A hair coloring method comprising: a. performing a plurality of light-scattering measurements upon a sample of hair such that for each light-scattering measurement, the sample of hair is illuminated from a different respective direction; b. comparing the results of the light-scattering measurements; c. in accordance with results of the comparing, computing an initial damage-state of hair of the sample by comparing the results of the light-scattering measurements; d. obtaining an initial color-state of the hair of the sample; and e. computing a hair-composition of a hair-coloring treatment, wherein: i. the hair-coloring composition comprises first and second artificial-colorants; ii. the rate of absorbance by hair-shafts of the first artificial-colorant exhibits a greater dependency upon an extent of damage to the hair-shafts than the rate of absorbance of hair-shafts of the second artificial-colorant; and iii. in response to a determining of a greater (lesser) extent of initial damage, a ratio between respective concentrations of the first and second artificial-colorants within the hair-coloring composition decreases (increases).

In some embodiments, the obtaining of the description of the initial damage state of the hair comprises: i. performing a plurality of light-scattering measurements upon a sample of hair such that for each light-scattering measurement, the sample of hair is illuminated from a different respective direction; and ii. comparing the results of the light-scattering measurements.

A hair coloring method comprising: a. computing or receiving an initial damage-state of a sample of hair; b. computing or receiving an initial color-state of the hair of the sample; and c. computing a hair-coloring composition that is predicted to transform the hair sample from the initial color-state to a target color-state such: (i) in response to a determining of a greater (lesser) extent of initial damage, a concentration of artificial-colorants within the computed coloring composition is reduced (increased); and/or (ii) in response to a determining of a greater (lesser) extent of initial damage, a lifting intensity of the hair-coloring composition is reduced (increased); and/or (iii) in response to a determining of a greater (lesser) extent of initial damage, a concentration of alkalizing agents (e.g. ammonia) in the hair-coloring composition is reduced (increased).

A hair coloring method comprising: a. performing a plurality of light-scattering measurements upon a sample of hair such that for each light-scattering measurement, the sample of hair is illuminated from a different respective direction; b. comparing the results of the light-scattering measurements; c. in accordance with results of the comparing, computing an initial damage-state of hair of the sample by comparing the results of the light-scattering measurements; d. obtaining an initial color-state of the hair of the sample; and e. computing a hair-coloring composition that is predicted to transform the hair sample from the initial color-state to a target color-state such that in response to a determining of a greater (lesser) extent of initial damage, a concentration of artificial-colorant(s) within the computed coloring composition is reduced (increased).

A method of measuring a hair damage-state comprises: a. subjecting a hair-shaft-aligned sample of hair to first and second light-scattering measurements such that: (i) the hair-shafts of the sample of hair are aligned with each other so as to collectively define a hair-alignment axis; (ii) for each light-scattering measurement, the hair is illuminated from a different respective hair-illumination direction; (iii) the hair-illumination directions and the hair-alignment directions are all co-planar; b. electronically comparing the results of the light-scattering measurements; and c. in accordance with the results of the comparing, computing a damage-state of hair of the sample.

In some embodiments, the light-scattering measurements are performed so that the collection direction(s) for each of the light-scattering measurements are the same.

In some embodiments, the light-scattering measurements are performed upon a sample of aligned hair-shafted that are aligned to define a hair-shaft alignment axis.

In some embodiments, collection direction(s) for each light-scattering measurement are in a plane (e.g. the y-z plane of FIG. 3A) that is perpendicular to the hair-shaft alignment axis (e.g. in FIG. 3A the hair-shaft-alignment axis is along the x-axis).

In some embodiments, the light-scattering measurements are performed so that scattered light for each light-scattering measurement is collected by the same collection device.

In some embodiments, the initial color-state is optically measured by an instrument including photodetector(s).

In some embodiments, the initial color-state comprises at least one of spectral data, and a color-space value (e.g. LAB value or RGB value).

In some embodiments, the comparing is performed by computing a ratio between respective intensities of light scattered by the hair during each of the scattering measurements.

In some embodiments, shafts of the hair-sample are aligned along an alignment axis.

In some embodiments, each of the beam-incidence-directions is substantially 0-degree-azimuth or substantially 180-degree-azimuth relative to the alignment axis and an azimuth-plane.

In some embodiments, the azimuth plane is perpendicular a perpendicular plane defined by the alignment axis and a hair-detector light-scattering direction for at least one of the light-scattering measurements.

In some embodiments, the azimuth plane is perpendicular to a perpendicular plane defined by the alignment axis and a hair-detector light-scattering direction for all of the light-scattering measurements.

In some embodiments, i. the light-scattering measurements are performed by a hair-reading device having a device-housing including a planar housing-window; ii. for each of the light-scattering measurements, source-light exits out of the device-housing via the planar housing-window to illuminate the hair and scattered-light from the hair enters into the device-housing via the planar housing-window; iii. the azimuth plane is defined as the plane of the housing-window.

In some embodiments, the first and second incidence directions subtend at least 10 degrees or at least 15 degrees or at least 20 degrees and/or at most 80 degrees or at most 70 degrees.

In some embodiments, an elevation-angle difference between the first and second incidence directions, as defined by the azimuth-plane, is at least 10 degrees or at least 15 degrees or at least 20 degrees and/or at most 80 degrees or at most 70 degrees.

In some embodiments, for each of the first and second reflection measurements, a detection-direction of light reflected by the aligned keratinous fiber(s) is substantially the same.

In some embodiments, a common photodetector respectively detects scattered light for each scattering measurement so as to generate each scattered-light-indicative electrical signal.

In some embodiments, the common photodetector is situated substantially at a zero-elevation angle relative to the aligned fiber(s).

In some embodiments, relative to the azimuth-plane, both the first and second incidence-directions have substantially the same azimuth value.

In some embodiments, relative to the azimuth-plane, an azimuth-angle difference between the first and second incidence-directions is substantially 180 degrees.

In some embodiments, response to the computing of the hair-coloring composition, automatically dispensing ingredients to achieve the adjusted concentration of artificial-colorant(s).

DETAILED DESCRIPTION OF EMBODIMENTS

Figure 1:
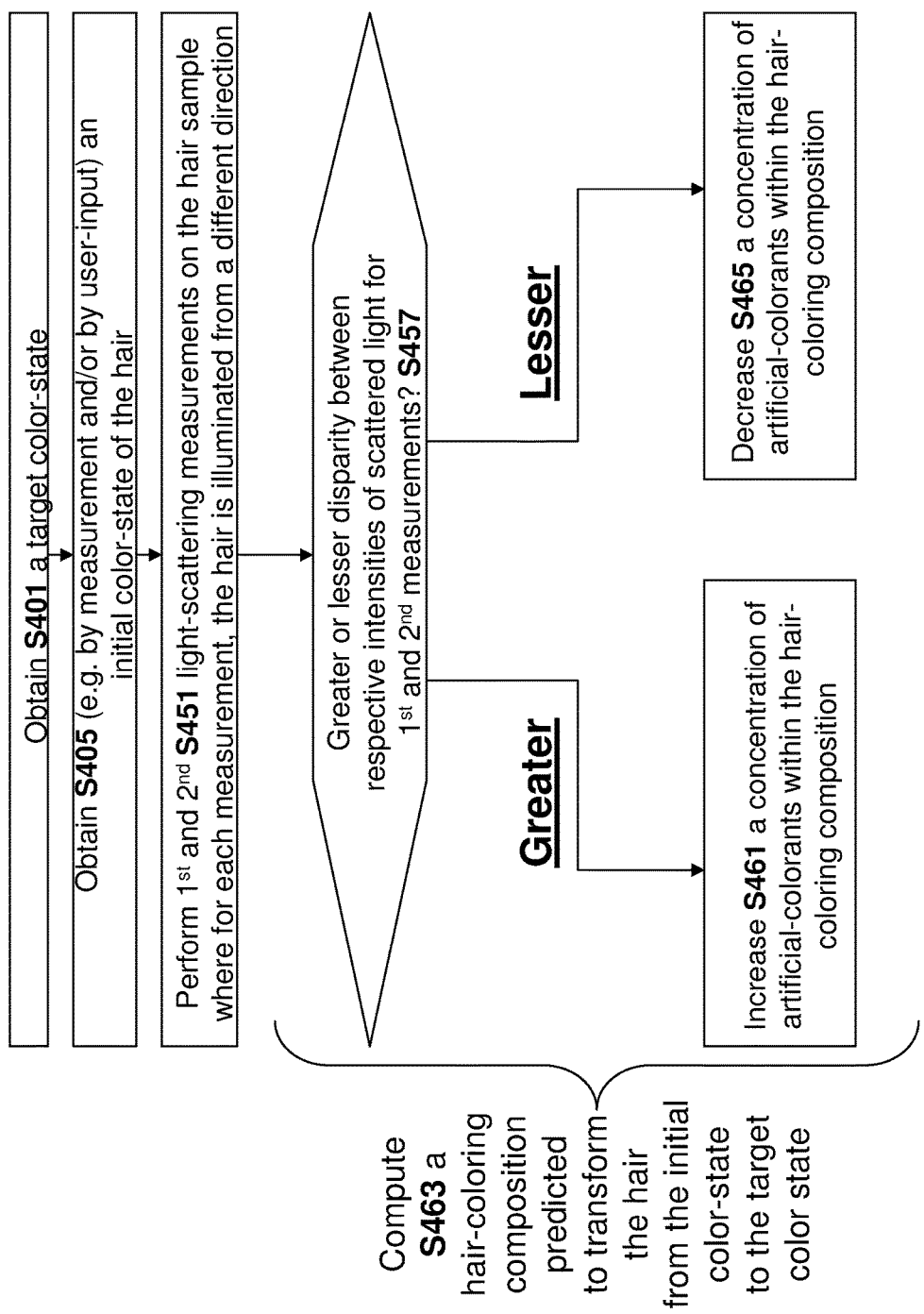
FIGS. 1-2, 8-9, 11, 12A-12B and 13-15 are flow-charts of methods related to analyzing hair and/or computing a customized hair-coloring treatment according to some embodiments.

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner including any combination of features and any combination of features can be included in any embodiment and/or omitted from any embodiments.

Preliminary Remarks

The present disclosure relates to coloring of keratinous fibers, more specifically to customized hair-coloring. In some embodiments, novel hair-coloring techniques which consider damage properties, and not only color-properties (e.g. LAB, spectrum) of 'initial hair' (i.e. hair before being subjected to a hair-coloring treatment—e.g. hair whose properties are measured by one or more optical instruments) are disclosed herein.

In some embodiments, although the primary determining factor for computing a hair-coloring treatment remains the initial hair-color status (e.g. spectral data, LAB value, RGB value, etc) and its relation to a hair-coloring target (e.g. expressed as an LAB value or in any other manner), a concentration of artificial colorants within the hair-coloring composition may be adjusted downwards when it is determined that the extent of previous damage to initial hair is relatively 'large.' Conversely, a concentration of artificial colorants within the hair-coloring composition may be adjusted upwards when it is determined that the extent of previous damage to initial hair is relatively 'small.'

Thus, some embodiments of the invention (see FIGS. 1-2 and 8-9) specify how to take a damage status of initial hair into account in order to transform a color status of hair from an initial status to a target hair-color status without "overshooting the target" or "undershooting the target."

Alternatively or additionally (see FIG. 11), for any hypothetical hair-coloring treatment, in addition to predicting a final hair-color status of hair after the hypothetical treatment, it is also possible to predict a final damage-status of hair. Because damage is cumulative, the final damage-status will be determined by the initial damage-status and the amount of collateral damage inflicted upon hair during the hair-coloring. As discussed below (see FIG. 11), by predicting the final damage-status of hair associated with a hair-coloring treatment, it is possible to perform one or more of the following: (i) alert the user if the hair-coloring treatment is predicted to transform the hair into a damage state that exceeds a 'maximum permitted' damage state; (ii) in such a case, present to a user an alternative target color state that differs from the preferred (e.g. user-specified target state) where (A) the alternative target color state is predicted to be 'compliant' with limitations upon a maximum amount of permitted damage to the hair; (B) the alternative target color state is as similar as possible to the 'preferred target state'— e.g. so as to minimize a distance in LAB (or any other) color space.

In theory, information about the hair-damage status of 'initial hair' may be provided in any manner to the computerized system for predicting a hair-coloring treatment. In one example, this information may be provided manually—e.g. a menu showing different damage states may be presented to a user (e.g on a display screen—e.g. a computer monitor or phone screen or tablet), and s/he may select the option that s/he 'subjectively' feels most closely describes the damage-state of the hair. In another example, an extent of damage may be computed from microscopy data using image-processing techniques.

Alternatively or additionally, a presently-described technique where hair is subjected to a plurality of light-scattering measurements may be employed. In some embodiments, hair is illuminated from first and second directions in the context of first and second light scattering measurements. For each light-scattering measurement, an intensity of light scattered by the hair (i.e. in one or more pre-determined scattering directions) is measured. If the intensity of the scattered light (i.e. in the scattering direction(s)) for each measurement is approximately equal (i.e. despite the fact that hair was illuminated from different directions), this indicates that the surface of each hair cuticle is relatively "smooth"—this is an indication that the hair has been previously damaged and that its damage status is 'high.' Conversely, if significant disparities in the intensity of the scattered light are detected, this indicates that the surface of each hair cuticle is relatively rough, and is indicative that the hair is undamaged or was only previously subjected to minimal damage. An additional discussion is provided below, with reference to FIG. 3A-3B.

When hair is subjected to first and second light-scattering measurements (i.e. respectively illuminating the hair from first and second directions), it is possible to compute a scattered-light-intensity disparity function describing differences in intensity of light scattered (i.e. in a particular direction) by the hair. This 'disparity' function (e.g. a ratio of intensities of scattered light) describes differences in the intensity of scattered light (i.e. the intensity that is scattered in a particular direction(s) defined by respective collection device(s)).

The above examples relate to 'first and second' light-scattering measurements and first and second illumination directions. It is appreciated that there is no limitation of exactly two light-scattering measurements and exactly two illumination directions—the terms "first and second" relate to two or more (at least two) including at least the first and second measurements (and illumination directions). Hair may be illuminated from more than two directions and at more than two illumination directions—results from more than two light-scattering measurements may be compared.

Experimental data linking a value of a scattered-light-intensity disparity function to (i) an extent of damage to the hair and (ii) an ability of hair-shafts to absorb artificial colorant change is presented herein. As will be discussed below, a sample of hair may be divided into a plurality of sub-samples, where each sub-sample is subjected to a different amount of damage. In this case, the hair is all the 'same hair' where the only difference is the amount of damage.

As will be discussed below with reference to FIG. 4, it was found that for sub-sets of hair that were subjected to a greater degree of damage, a value of a scattered-light-intensity disparity function was lower—i.e. damaging the hair reduced a disparity between intensities of scattered light collected from the first and second hair-scattering measurements (e.g. in a particular direction (single collector)).

Figure 5:
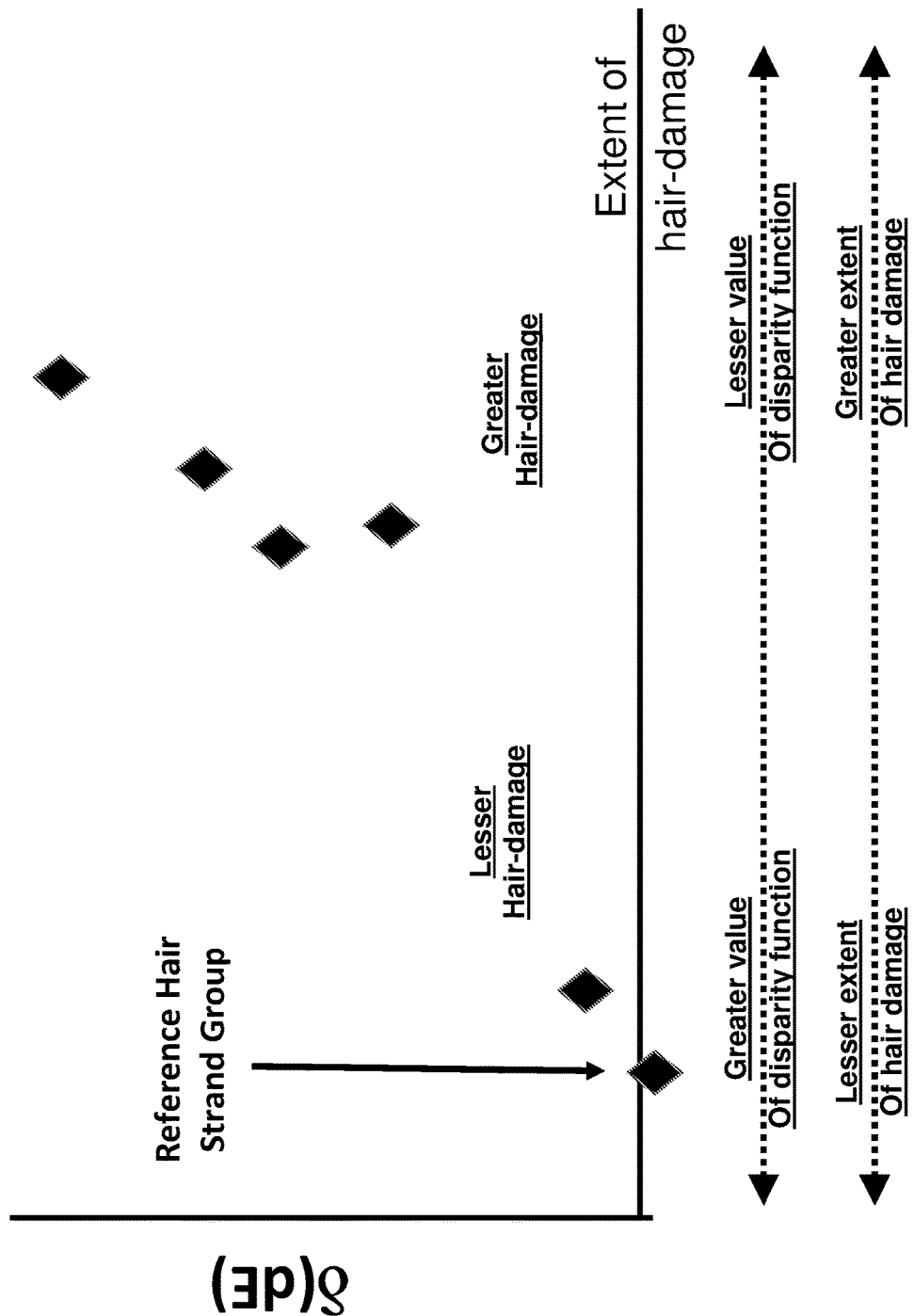

Additional experimental data is presented below with reference to in FIG. 5. In the experiments of FIG. 5, a sample of hair is divided into subsets of the sample. Before any coloring, hair of each subset is either left undamaged or subjected to a different extent of damage. Subsequently, all hair is subjected to the same hair-coloring (i.e. dying) process. It was observed that initial hair which is damaged to a greater extent is more affected by dying (i.e. exhibits a bigger change in color) than hair which is undamaged or only minimally damaged.

Figure 10:
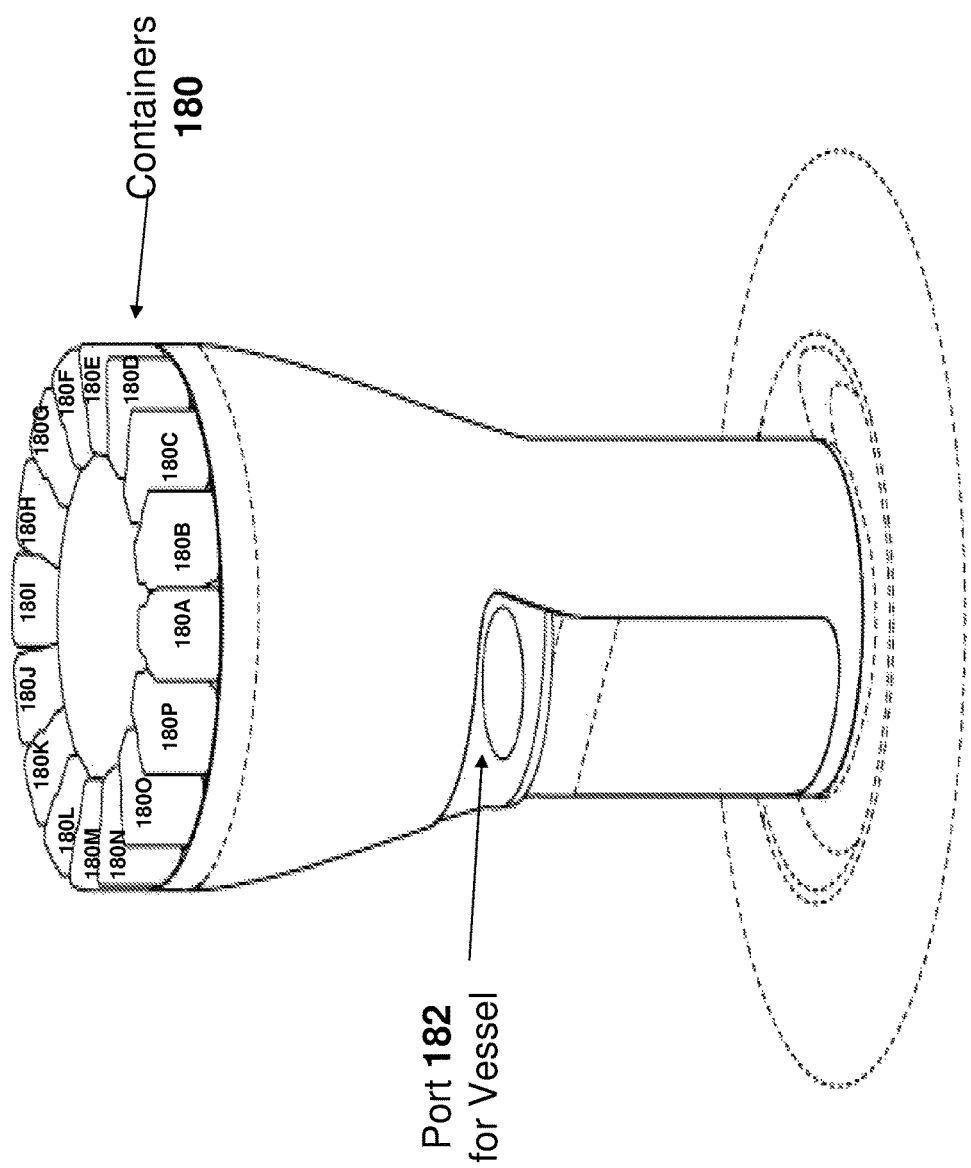
FIG. 10 illustrates a dispenser device.

As noted in above the 'Background,' in recent years there have been disclosures of dispenser devices that dispense ingredients for a hair-coloring solution according to computed predictions of a final color-state One such dispenser device is illustrated in FIG. 10.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

For the present disclosure, the term 'shaft' refers to an individual hair and is not limited to the 'shaft portion' (i.e. away from the root portion) of an individual hair.

"Damage" to hair (or 'hair damage') refers to anything that irreversibly changes (i) the mechanical structure or properties of the hair and/or (ii) the chemical status of natural molecules within hair. The "natural molecules" of hair are natural pigments (e.g. melanin species) and proteins of the hair (e.g. fibrous structural proteins such as keratin) that give hair its structure. The "chemical status" of a natural molecule relate to its concentration within the hair or its molecular structure. Examples of irreversibly changing a "chemical status of natural molecules" thus include (i) irreversibly reducing a concentration of a natural pigment (e.g. melanin species) and (ii) irreversibly modifying a molecular structure, for example, by protein denaturation.

A 'damage status' refers to a status of hair reflecting previous damage to the hair.

Causes of 'damage' to hair include but are not limited to exposure to UV light, heating of hair (e.g. during a previous hair-coloring process), exposing hair to dry conditions, mechanical damage (such as combing), exposing hair to chemical materials (such as chlorine) and subjecting hair to a curling treatment.

For the present disclosure, concentration of 'artificial colorants' within the hair are defined as to not relate to the 'damage status' since they do not relate to chemical status of natural molecules or to a mechanical state of the hair. However, dying hair with artificial colorant might cause a certain amount of 'collateral damage.'

The term "color-imparting agent" refers to a hair-coloring agent (e.g. for example, for permanent hair-coloring) or to an ingredient thereof.

When a sample of hair is illuminated, a beam of light is incident upon the hair—although not illustrated as such in the figures (which are schematic), the skilled artisan will appreciate that a beam (e.g. schematically illustrated as 1020A-102D in FIGS. 3A-3B) has some sort of divergence and as such there is not a single 'illumination direction.' The term 'illumination direction' relates to a representative direction/chief ray for the incident beam of light incident upon the hair.

In some embodiments, hair is illuminated from first and second directions, and an intensity of scattered light is measured. Unless specified otherwise, a light scattering 'measurement' refers to measuring the intensity of light scattered in one or more specific 'collection directions' (referred to below as 'scattered-light-to-detector' direction 1024) and not the overall intensity of all light scattered in all directions—e.g. if there is more than one collection direction, each collection is associated with a different respective collector device (e.g. including collection optics and detector).

The term 'collection direction' is the direction from which the collection optics collects light scattered by the hair. One example of a 'collection direction' is given in FIGS. 3A-3B as 1024. Preferably, when scattering measurements are compared (e.g. to compute a 'disparity' between intensities of scattered light—see, e.g. S451-S457 or S409-S417 (in some embodiments thereof) the scattered light is collected in the same collection direction (or set of collection directions if there are multiple detectors) in each of the light-scattering measurements. For example, scattered light (i.e. scattered from hair in the first and second light-scattering measurements) is collected by the same collection device (or set of collection devices) for each of the measurements.

A 'comparison function' relates to a comparison between intensities of collected light.

When the intensity of the light for two scattering measurements (i.e. in comparable collection direction(s)) are compared, the intensity may be equal or may differ from each other. A 'disparity' (or disparity function) quantifies how much the intensities different from each other—for intensity values A and B, examples of 'disparity functions' include A-B, A/B, B/A and B-A. Thus, if a disparity function if A/B is selected, a value of 1 indicates no disparity, and the extent of disparity increases as the value A/B deviates from 1 (i.e. values greater than 1 'deviating' towards infinity, and values less than 1 'deviating' towards infinity).

A "substantial majority" means at least 75%. In some embodiments, a 'substantial majority' is at least 90% or at least 95% or at least 99%. Unless specified otherwise, a 'majority' means 'at least a majority.' Unless specified otherwise, 'at least a majority' means that, in some embodiments, the 'majority' is at least a substantial majority—i.e. at least 75% or at least 90% or at least 95% or at least 99%.

A 'hair-shaft-aligned sample' of hair is when shafts of the sample are aligned to define an alignment axis—e.g. see 1010.

Electronic circuitry may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

A 'hair-coloring treatment' is any treatment which modifies the color of hair shafts. Examples of hair-coloring treatments include hair-dying treatments (e.g. based upon artificial colorants) and bleaching. Examples of hair-dying treatments are temporary, demi-permanent, semi-permanent or permanent hair-dying (e.g. oxidative hair-dying).

The term 'user-target' typically includes to a target color shade—e.g. expressible as a value in color-space such as Hunter Lab color space or any other color space. In addition to a target color shade, user-target data may also include some other desired characteristic of any proposed hair-treatment—e.g. a treatment of 'roots-only' as opposed to 'entire-hair-shaft,' a maximum treatment time, etc.

A plurality of hypothetical or 'candidate' hair-treatment protocols may be analyzed and considered. A 'hair-treatment' may refer to any one of: (A) content of a hair-coloring composition (or more than one hair-coloring composition which may be applied sequentially or simultaneously—for example, a dye-containing composition and a bleaching composition) to be applied to the hair and/or (B) other treatment parameters—e.g. treatment durations, treatment temperature. Computing or specifying a 'hair-treatment' may include specifying at least absolute or relative quantities or 'loads' (i.e. expressed in molar terms, or as weights, or a volumes, or in any other manner known in the art) of one or more hair-coloring agents of a hair-coloring composition (e.g. a 'multi-agent' composition). The term 'hair-coloring agent' may include an artificial colorant/dye, an oxidizer, an alkalizer or an other substance used in the art for temporary, semi-permanent, demi-permanent or permanent hair-coloring. A hair-coloring agent may be in any phase or form, including but not limited to liquid, gel, mouse, cream, solid, powder, tablet, or any other form known in the art. Optionally, a 'hair-treatment' also includes data relating to treatment time, treatment temperature, multi-stage treatments or any other parameter of treatment. For example, a hair-treatment may entail production of multiple distinct combinations of hair-coloring agents—e.g. a coloring mixture and a bleaching mixture which are applied in different stages.

For the present disclosure, the term 'hypothetical' and 'candidate' are used interchangeably and refer to possible treatments that may or may not be actualized.

Figure 2:
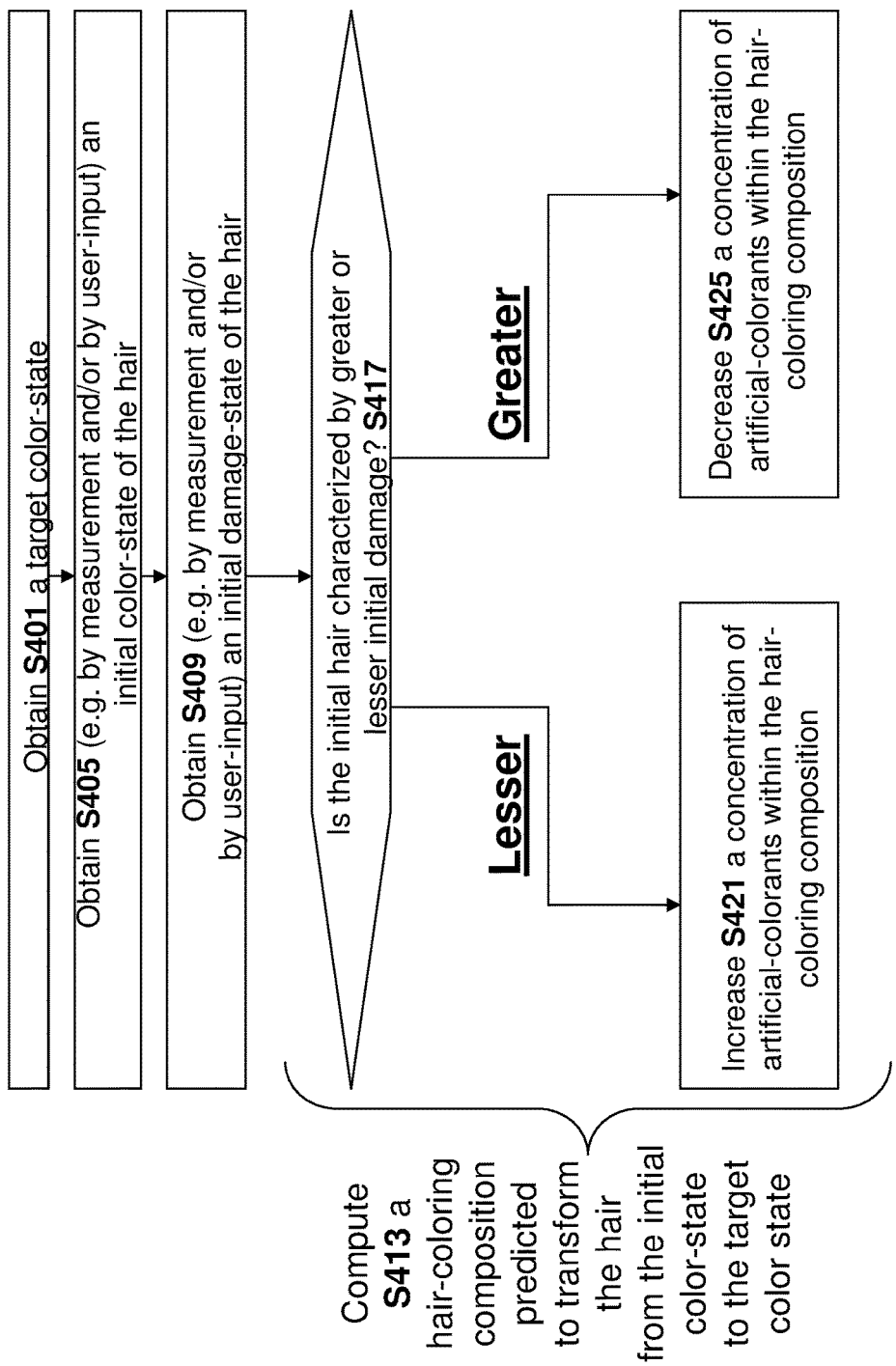

A Discussion of FIGS. 1-2

In step S401 of FIG. 1, a target color state is received and stored (e.g. in volatile and/or non-volatile computer-readable storage). The target color state relates to a selected shade or color—e.g. a user desires to color his/her hair to the selected shade or color. This may be expressed as an LAB value or in any other manner known in the art.

In step S405, data describing the initial color-state (e.g. spectral data or LAB value) is obtained—either manually by user-input or by measuring the hair (e.g. using a hair-reader device such as that disclosed in PCT/IB2012/051351 or PCT/IL2014/050850, both of which are incorporated herein by reference).

Figure 3A:
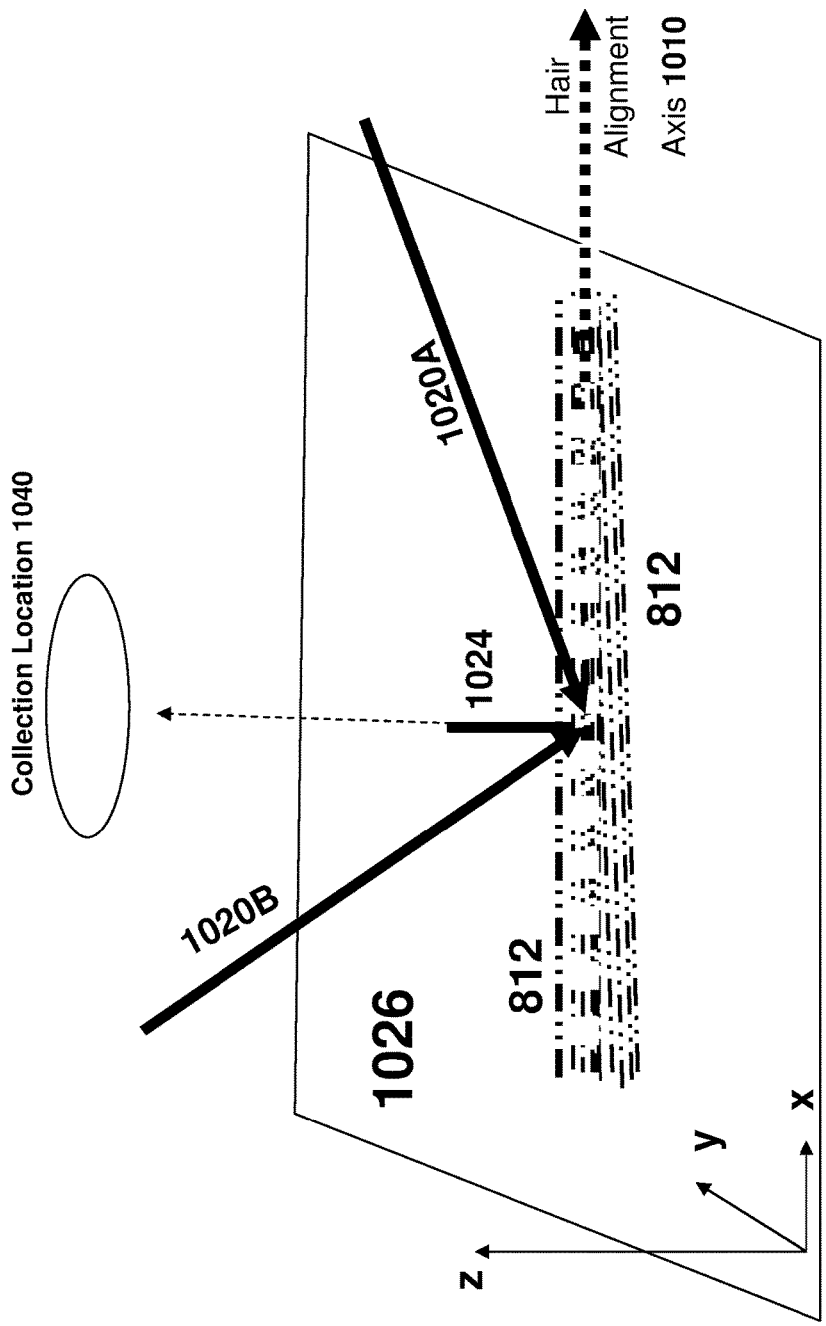
FIGS. 3A-3B, 6, 7A-7B relate to the performance of light-scattering measurement upon hair (e.g. aligned hair-shafts) according to some embodiments.
Figure 3B:
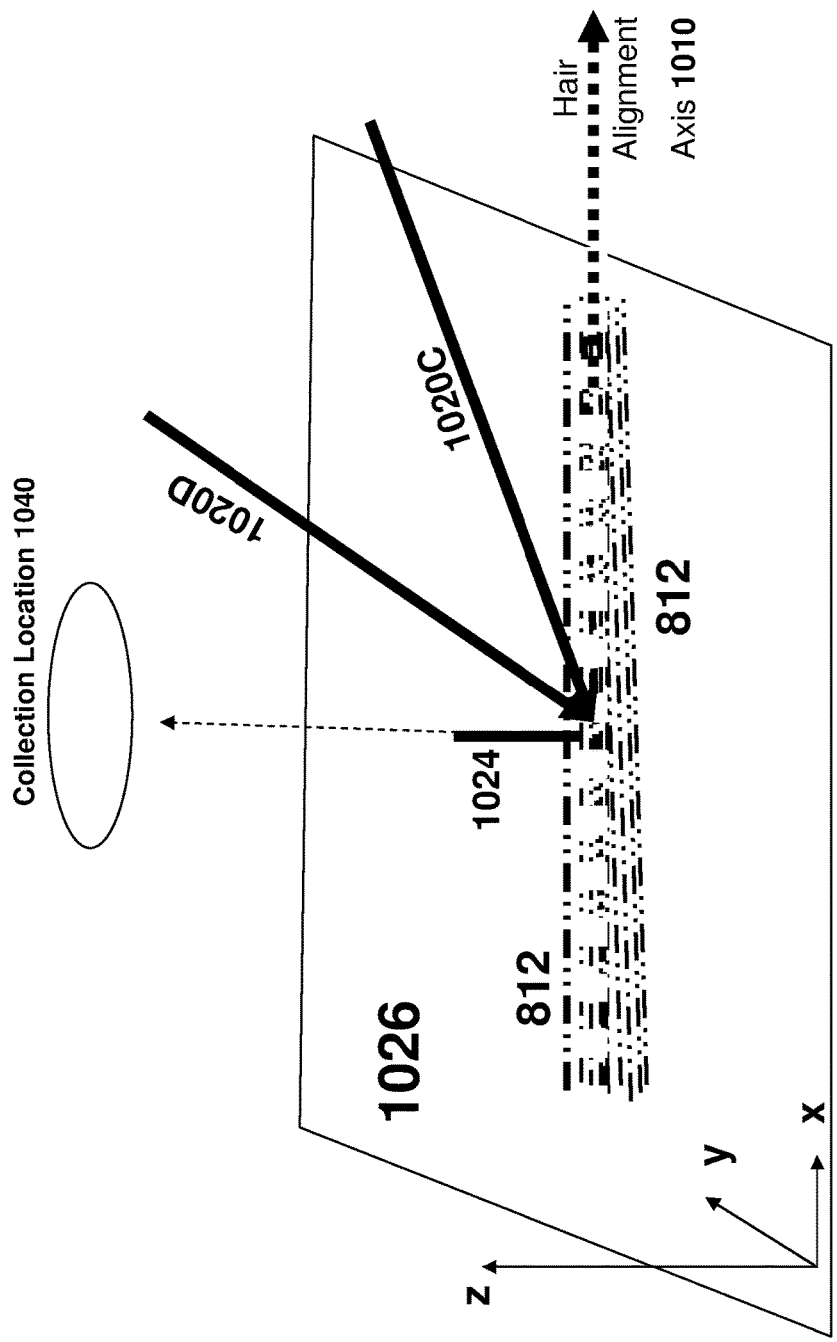

In step S451, the sample of hair (e.g aligned hair-shafts that are aligned to define a hair-shaft alignment axis 1010) is subjected to first and second light scattering measurements where hair is respectively illuminated from first and second illumination directions (for example, directions 1020A and 1020B of FIG. 3A; for example, directions 1020C and 1020D of FIG. 3B). Each scattering measurement records an intensity of light scattered in one or more "collection" directions (defined above—e.g. direction 1024 of FIGS. 3A-3B). As noted above, for the purpose of comparison, it is preferred that the collection direction(s) for each light-scattering measurement are comparable.

The results of the light scattering measurements are compared in step S457, and a 'disparity function' (defined above) is computed describing. In the event that the disparity function is relatively 'large' (e.g. indicating that the hair is relatively undamaged), a hair-coloring composition (i.e. predicted to transform hair from the initial color-state to the target color-state) is computed to 'upwardly' adjust S461 a concentration of artificial colorants within the hair-coloring composition. This is because undamaged hair is considered relatively 'robust' when treated with artificial colorants (and is less absorbent of colorant) and greater quantities of hair-coloring composition are required to achieve a requisite change in color.

Conversely, in the event that the disparity function is relatively 'small' (e.g. indicating that the hair has in fact been damaged), a hair-coloring composition (i.e. predicted to transform hair from the initial color-state to the target color-state) is computed to 'downwardly' adjust S465 a concentration of artificial colorants within the hair-coloring composition. This is because damaged hair is not very 'robust' when treated with artificial colorants (and is more absorbent of colorant) and lesser quantities of hair-coloring composition are required to achieve a requisite change in color.

Steps S457, S461 and S465 are performed in the context of step S463 whereby a hair-coloring composition predicted to transform the hair from the initial color-state to the target color state is computed.

FIG. 2 is similar to FIG. 1 except it is noted that the scattering disparity is not the only way to obtain data descriptive of hair-damage. Thus, in FIG. 2, the initial damage state may be obtained in any manner in step S409. In step S417, it is determined if the hair is characterized by lesser damage (i.e. in which case the concentration of artificial colorants are increased in step S421) or by greater damage (i.e. in which case the concentration of artificial colorants are decreased in step S425).

FIGS. 1-2 do not specify by how much the concentration of artificial colorants should be increased. However, in one non-limiting example, this can be computed as follows: a training set of is created by damaging the same hair to different extents—for each extent, the hair damage and/or 'disparity function' may be computed.

This yields a sample set of hair where each sample is substantially identical except for extent of previous damage (and/or a value of the 'disparity function'). Each sample is then subjected to an identical dying process—i.e. at the same conditions and the same concentration of artificial colorant. After the dying processes, the 'post-dying' hair color-state of each sample is measured—e.g. by a spectrometer or a colorimeter or in any other manner. This may, for example, be converted to a respective post-dying LAB value for each sample. It will be found that: (i) for the undamaged samples (or those subjected to minimal damage), the magnitude of change in color is less than for the pre-damaged samples; and (ii) for the samples exhibiting a 'high value' of the disparity function), the magnitude of change in color is less than for the samples exhibiting a 'low value' of the disparity function.

This describes subjecting a sample of hair of the same hair-dying process, and recording the outcomes (i.e. change in color—e.g. by change in LAB values). This can repeated for different concentrations of artificial colorants. Thus, it will be found that (i) hair that has been damaged to a greater extent and dyed by a composition having a lower concentration of artificial colorants and (ii) hair that has been damaged to a lesser extent and dyed by a composition having a higher concentration of artificial colorants exhibit the same color change magnitude.

Thus, there is an equivalent color change between these two samples of hair. This is one example of a 'relation between an extent of damage' and a concentration required to bring about a specific change in color.

The inventors have found that the effect does not have the same extent for all artificial colorants—for some colorants, the relation between the extent of hair damage (or the value of the disparity function) and the change observed in hair-color after dying is a relatively 'strong one'—i.e. after hair is damaged, an equivalent concentration of hair-dye (in an equivalent dying process) brings about a much large change in hair-color compared to undamaged hair. However, for other colorants, the relation may be a relatively weak one—the modification in hair-color, for these colorants, does not strongly depend the extent of hair-damage.

In order to compute how much a concentration of artificial colorant needs to be adjusted to bring about a requisite change in hair-color, it is possible to first collect data from many types of hair and for many types of dyes, and for many different concentrations of hair-dye. At a later time, this can serve as a training set or the basis of a look-up table. When a new sample of hair is encountered, the damage (and/or disparity function) is determined, and information from the training set (or look-up table) may be used to compute how much the concentration of artificial colorant (or a specific type of colorant) needs to be adjusted.

A Discussion of FIGS. 3A-3B, 6 and 7A-7B

Figure 6:
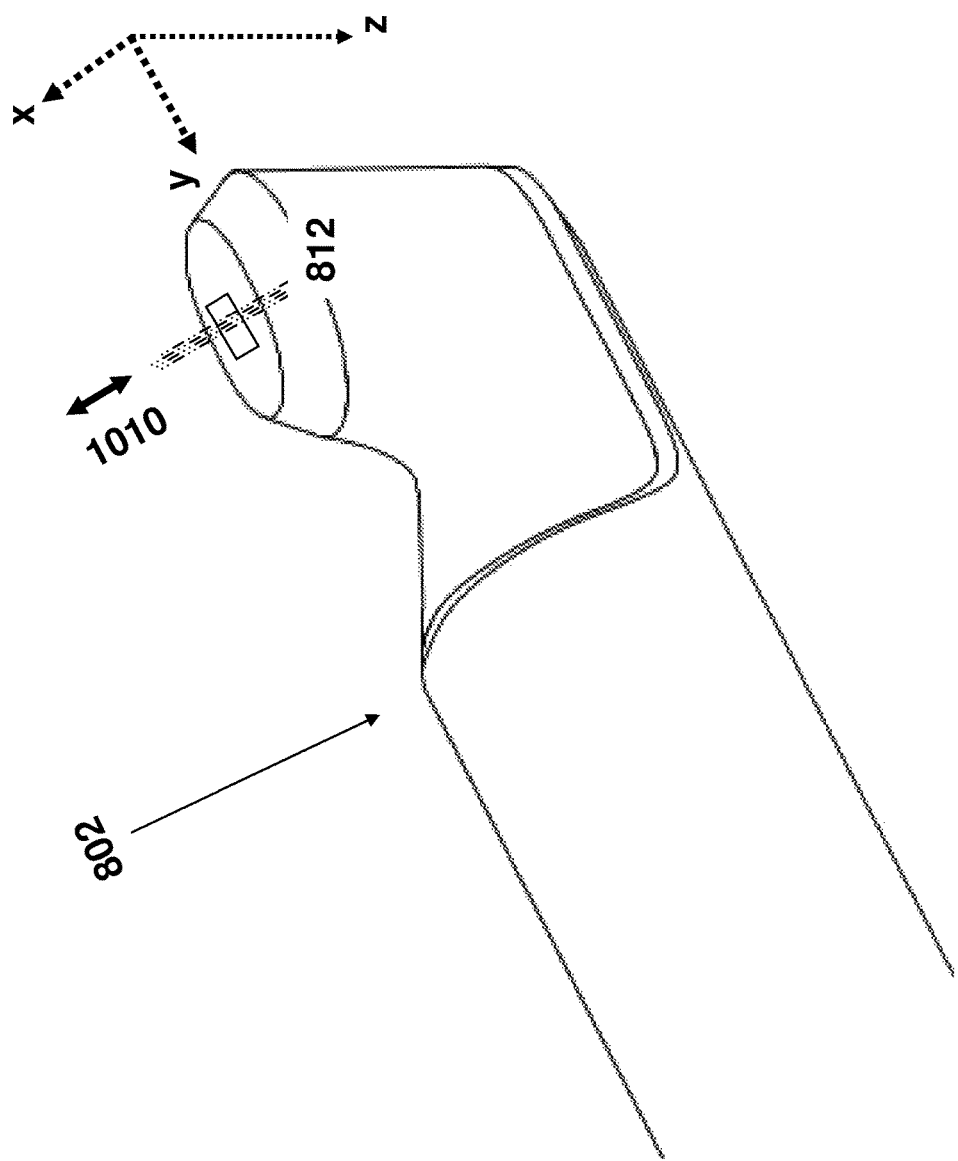

FIG. 6 illustrates an exemplary hair-reader 800 in accordance with some embodiments. Hair-reader 800 includes a housing 804 (e.g. opaque) and a window 808. In FIG. 6, a plurality of keratinous fibers 812 are substantially aligned along an alignment axis 1010 which corresponds to the 'x' axis.

In some embodiments, one or both of (i) a light source(s) and/or (ii) light detector are disposed within housing 804.

Figure 7B:
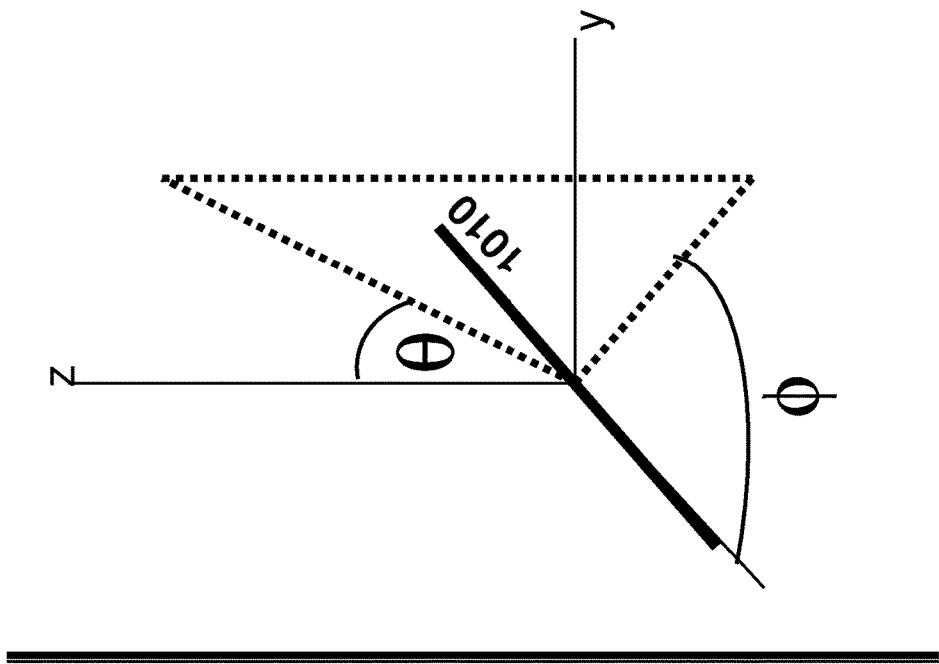
Figure 7A:
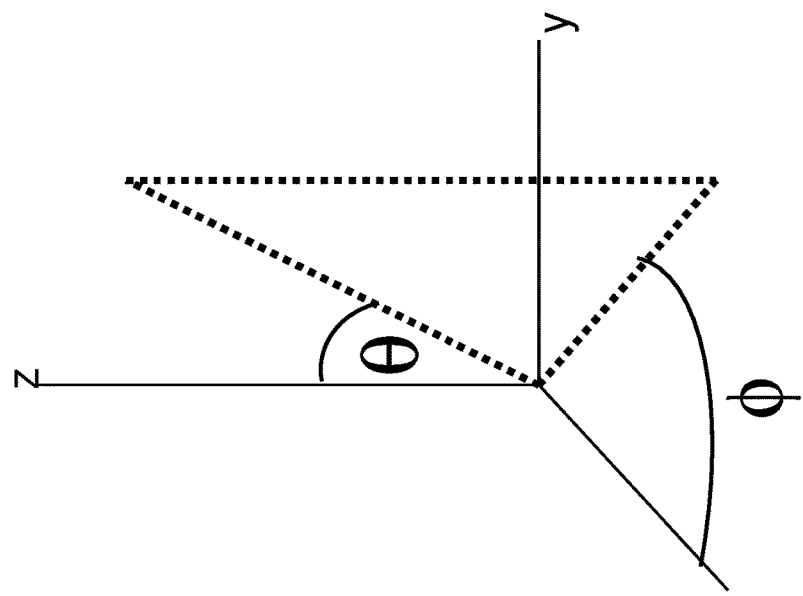

FIGS. 7A-7B illustrate a polar coordinate system where the x and y-axes are in the 'azimuth' reference plane or 'azimuth plane'. As shown in FIG. 7B, for the present disclosure alignment axis 1010 is taken to correspond with the x axis. In one non-limiting example, the 'azimuth plane' is defined by window 808.

Alternatively or additionally, the 'azimuth plane' may be defined in terms of a 'scattered-light-to-detector' direction 1024 that is the initial direction (i.e. immediately after scattering by the hair) of scattered light on an optical path from the hair (i.e. at a scattering location) to a detection location 1040 (i.e. a location of a detector for detecting scattered light).

FIG. 3A illustrate incident directions of two beams of light (e.g. incoherent light)—the first beam of light is incident upon the aligned keratinous fibers 812 from a first beam-incidence direction 1020A and the second beam of light is incident upon the aligned keratinous fibers 812 from a beam-second incidence direction 1020B. In the polar coordinate system defined so that the hair-elongate axis 1010 is along the x-axis, each incidence direction 1020A, 1020B respectively defines both an azimuth-angle value and an elevation-angle value.

In the example of FIG. 3A, a difference between (i) an azimuth-angle value of the first incidence direction 1020A and (ii) an azimuth-angle value of the second incidence direction 1020B is 180 degrees—thus, first 1020A and second 1020B incidence directions are 'opposite directions with respect to azimuth.'

In contrast, in the example of FIG. 3B both directions have the same azimuth-angle value.

In the example of FIGS. 3A-3B, light is detected at a 'detection location' 1040.

As noted above, the azimuthal plane may be defined in terms of a 'scattered-light-detector' direction which is defined relative to detection location 1040. In FIGS. 6A-6B, the 'scattered-light-to-detector' direction is labeled as 1024. When the azimuthal plane is defined in terms of a 'light-scatter' direction, (A) a 'perpendicular plane' is defined as the plane including both (i) hair-alignment axis 1010 and (ii) 'scattered-light-to-detector' direction 1024; and (B) azimuth plane 1026 is perpendicular to the 'perpendicular plane.'

When a direction is 'azimuthal' the direction has an azimuth value of 0 or 180 degrees—the corresponds to within the perpendicular plane.

When a direction is 'substantially zero-degrees-azimuth' this means that an azimuth value of the direction is between −a degrees and +a degrees, wherein a is a positive number and a value of a is at most 20 degrees or at most 15 degrees or at most 10 degrees or at most 5 degrees.

When a direction is 'substantially 180-degrees-azimuth' this means that an azimuth value of the direction is between 180−a degrees and 180+a degrees, wherein a is a positive number and a value of a is at most 20 degrees or at most 15 degrees or at most 10 degrees or at most 5 degrees.

When a direction is 'substantially azimuthal' the direction is either 'substantially zero-degrees-azimuth' or 'substantially 180-degrees-azimuth.'

When two directions are 'substantially opposite directions with respect to azimuth' this means that a difference between (i) an azimuth value of the first direction and (ii) an azimuth value of the second direction is 180−a degrees and 180+a degrees, wherein a is a positive number and a value of a is at most 20 degrees or at most 15 degrees or at most 10 degrees or at most 5 degrees.

When two directions have substantially the same azimuth value, an absolute value of a difference in azimuth values of the two direction is at most a wherein a is a positive number and a value of a is at most 20 degrees or at most 15 degrees or at most 10 degrees or at most 5 degrees.

With reference to FIG. 3A, it is noted that an absolute value of a difference between an (i) an elevation-angle value of direction 1020A and (ii) an elevation-angle value of direction 1020B is non-zero—for example, at least 10 degrees or at least 15 degrees or at least 20 degrees and/or at most 80 degrees or at most 70 degrees or at most 60 degrees.

Similarly, with reference to FIG. 3B, it is noted that an absolute value of a difference between an (i) an elevation-angle value of direction 1020C and (ii) an elevation-angle value of direction 1020D is non-zero—for example, at least 10 degrees or at least 15 degrees or at least 20 degrees and/or at most 80 degrees or at most 70 degrees or at most 60 degrees.

According to FIG. 3A, the aligned keratinous fiber(s) 812 are subjected to first and second light-scattering measurements such that: i. for each of the measurements, a respective beam of light is incident upon the aligned keratinous fiber(s) 810 at first 1020A and second 1020B incidence directions; ii. the first incidence-direction 1020A is substantially 0-degree-azimuth; and (iii) the second incidence-direction 1020B is substantially 180-degree azimuth. In the non-limiting example, for both scattering measurements, scattered light is collected by a common collection-optics device situated at a collection location 1040.

According to FIG. 3B, the aligned keratinous fiber(s) 812 are subjected to first and second light-scattering measurements such that: i. for each of the measurements, a respective beam of light is incident upon the aligned keratinous fiber(s) 810 at first 1020C and second 1020D incidence directions; ii. the first incidence-direction 1020C is substantially 0-degree-azimuth; and (iii) the second incidence-direction 1020D is substantially 0-degree azimuth. In the non-limiting example, for both scattering measurements, scattered light is collected by a common collection-optics device situated at a collection location 1040.

Figure 4:
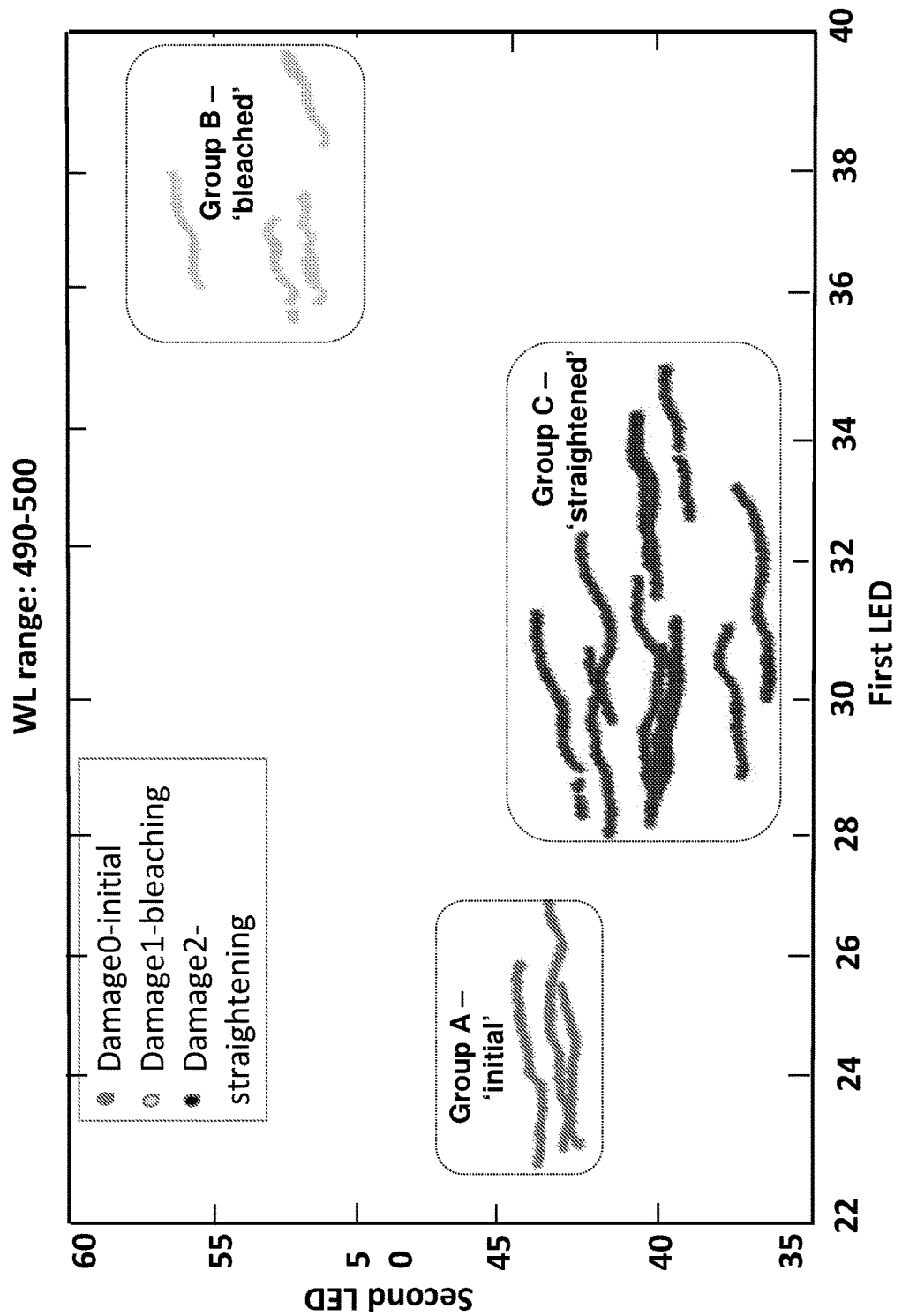
FIGS. 4-5 present results of experiments.

A Discussion of FIGS. 4, 5A-5B Experimental Data

The present inventors have conducted experiments using a system similar to that described in FIG. 3A—results are described presented in FIGS. 4-5. In the example of FIG. 4, hair is not subjected to any coloring process. In the example of FIG. 5, hair is subjected to a coloring process.

In the example of FIG. 4, first and second light-scattering measurements were respectively performed (for at least one wavelengths—for example, at multiple wavelengths) an a sample of hair. For each experiment, a respective 'scattering-measurement comparison function' SMCF and/or 'disparity function' (e.g. related to a ratio or quotient of between respective intensities of scattered light for the first and second measurement of the experiment) of the intensity of scattered light (e.g. at wavelength(s) in the 490 nm-500 nm range) was computed.

FIG. 4 describes a correlation between (i) 'hair-type' of the initial hair that is subjected to the plurality of scattering measurements (and for which); and (ii) a physico-chemical state of the initial hair. Although not a requirement of the invention, in the experiments of FIG. 4 were 'spectral' measurements—i.e. for each incident-direction, measurements were acquired over a plurality of wavelengths. Each point in FIG. 4 represents by a pair of measurements at a single wavelength—a first light-scattering measurement (i.e. from a first LED illuminating hair from a first illumination direction 1020A) and a second light-scattering measurement from a second LED illuminating hair from a first illumination direction 1020B. For a single group of hair-strands, a spectral measurement over multiple wavelengths (i.e. a first measurement at a first direction 1020A and a second measurement at a second direction 1020B) appears as a one-dimensional 'squiggly' curve. There are 3 such curves in Group A and four such curves in Group B.

Hair-strands in 'group A' were not subjected to any physical treatment (i.e. were not pre-damaged) and were just 'pure natural' hair-strands. Hair-strands in group B were subjected to a bleaching treatment (i.e. which damages hair). Hair-strands in group C were subjected to a straightening treatment (i.e. which also damages hair).

It is possible to select MAX(B/A,A/B) as a disparity function—when this is exactly unity, the disparity function is relatively small.

For group A, the disparity function is about 44/25 or 1.76, for group B the ratio is about 54/37 or about 1.46 and a for group C the ratio is about 40/31 or about 1.3. This indicates that the undamaged hair (e.g. Group A) has the greater value of the disparity function MAX(B/A,A/B) and the disparity function for the more damaged hair (i.e. bleached or straightened) is significantly less.

Additional experimental data is presented below with reference to in FIG. 5. In the experiments of FIG. 5, a single type of hair from a single sample is divided into subsets of the sample. Before any coloring, hair of each subset is either left undamaged or subjected to a different extent of damage. Subsequently, all hair is subjected to the same hair-coloring (i.e. dying) process.

Each subset is represented by a different data-point in FIG. 5. The x axis indicates the extent of hair-damage where more damaged hair has a 'higher value' on the x axis and less damaged hair has a lower value. Similarly, as shown in FIG. 5, hair for which a greater value of a disparity function may be measured has a 'lower value' on the x axis and hair for which a lower value of a disparity function may be measured has a 'higher' value' on the x axis.

The present inventors have conducted experiments indicating that an extent of color change (e.g. expressed as dE values describing a magnitude of a color-change vector in color space—for example, Hunter LAB color space) for each sample of hair. The y axis relates to change in color.

In FIG. 5, instead of graphing 'dE' on the y-axis, a reference group of hair-strands strands-ref was considered for which a magnitude of the hair-change vector in color space $dE_{REFERENCE-HAIR-STRAND-GROUP}$ Thus, for all other strands, instead of graphing $dE_{HAIR-STRAND-GROUP}$ for each hair-strand-group, FIG. 5 graphs $\delta(dE_{NON-REFERENCE-STRAND-GROUP})= dE_{HAIR-STRAND-GROUP} - dE_{REFERENCE-HAIR-STRAND-GROUP}$.

By definition, the value for the reference hair strand group (identified with an arrow in FIG. 5).

As illustrated in the figures, there is a clear correlation between extent of damage and $\delta(dE_{NON-REFERENCE-STRAND-GROUP})$—in general, for higher values of damage to 'initial hair' are correlated to higher values of $\delta(dE_{NON-REFERENCE-STRAND-GROUP})$ indicating that damaged hair better absorbs artificial colorant.

Thus, the upward slow of FIG. 5 indicates that initial hair which is damaged to a greater extent is more effected (i.e. exhibits a bigger change in color) by artificial colorant than hair which is undamaged or only minimally damaged.

In accordance with FIGS. 5-6, is now disclosed for the first time that the scattering-measurement-comparison function (or disparity function) from the first and second scattering measurements may function as a 'physical-mathematical probe' of the initial hair in order to predict and least one of (i) the extent of color-change associated with a candidate/hypothetical hair-coloring treatment (or composition for hair-coloring treatment) and/or (ii) an amount or 'load' of an ingredient hair-coloring treatment required to achieve an objective to modify hair color from an initial color-state to a target color-state.

Figure 8:
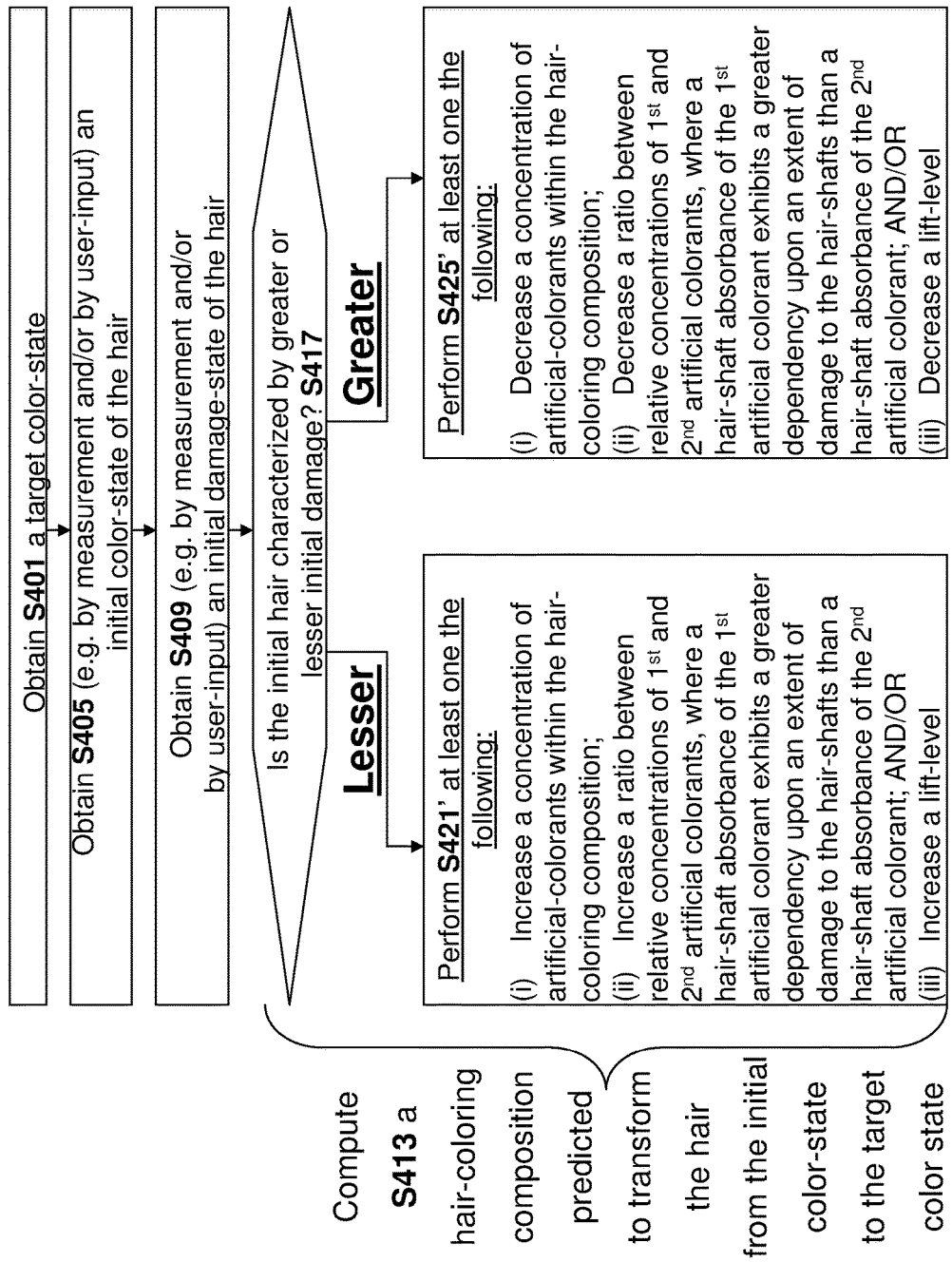
Figure 9:
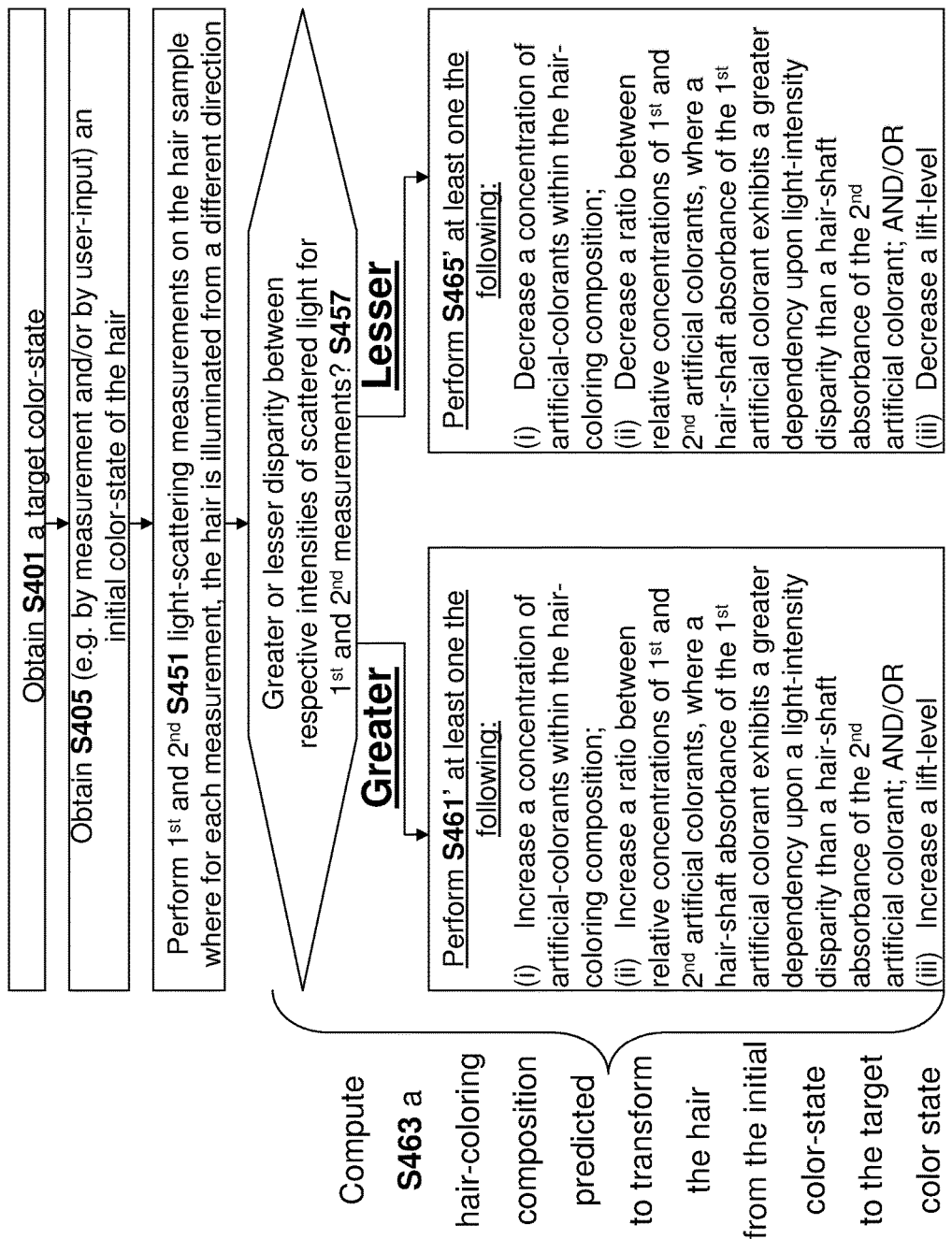

A Discussion of FIGS. 8-9

FIGS. 8-9 are similar to FIGS. 1-2. However, FIGS. 8-9 relate to the fact that the influence of hair-damage upon the ability of hair to absorb artificial colorants (i.e. where damaged hair more readily absorbs artificial colorant and therefore requires a lower concentration) is not the same for all colorants.

For some colorants, the relation between the extent of hair damage (or the value of the disparity function) and the change observed in hair-color after dying is a relatively 'strong one'—i.e. after hair is damaged, an equivalent concentration of hair-dye (in an equivalent dying process) brings about a much large change in hair-color compared to undamaged hair. However, for other colorants, the relation may be a relatively weak one—the modification in hair-color, for these colorants, does not strongly depend the extent of hair-damage. Thus, in step S425', in some embodiments, in response to detecting a greater extent of initial hair damage, a concentration of both first and second artificial colorants may be reduced. However, if the 'dependency' of the ability to absorb hair-colorant upon extent of hair-damage is stronger for a first colorant than for a second colorant, the concentration of the first artificial colorant may be reduced to a greater extent than for the second artificial colorant. In this case, in response to a determining of a greater extent of damage, a ratio between relative concentrations of the first and second artificial colorants is reduced, where, as mentioned above, the first artificial colorant exhibits a greater dependency upon an extent of damage to the hair shafts (i.e. of 'initial hair) than the second artificial colorant.

Alternatively or additionally, a lift level (i.e. related to whitening of the hair—e.g. by sulfate or bleach) of the hair-coloring composition may be decreased in response to a determining of a greater extent of damage—i.e. less lift (e.g. lower concentrations or less 'powerful' lifting agents) may be required.

Step S421' is the opposite case of that described for step S425'.

Steps S461' and S465' are analogous to steps S421' and S425' but they relate specifically to a disparities in intensities of scattered light.

A Discussion of FIG. 10

In different embodiments, according to and/or in response to a computation of a hair-coloring protocol and/or composition, respective quantities of hair-coloring agent, for a plurality of hair-coloring agents. One non-limiting example of a dispenser of hair-coloring agents is illustrated in FIG. 10. In this non-limiting example, different respective hair-coloring agents are disposed in each container of a plurality of containers 180A-180Q. In response to the, according to and/or in response to a computation of a hair-coloring protocol and/or composition, for at least 2 or at least 3 or at least 4 or at least 5 or at least any number of hair-coloring agents, respective quantities of each hair-coloring agent are dispensed into a vessel (not shown) located in port 192.

In some embodiments, the dispenser is automatic and includes electronic circuitry for regulating quantities of hair-coloring agents that are dispensed.

Figure 11:
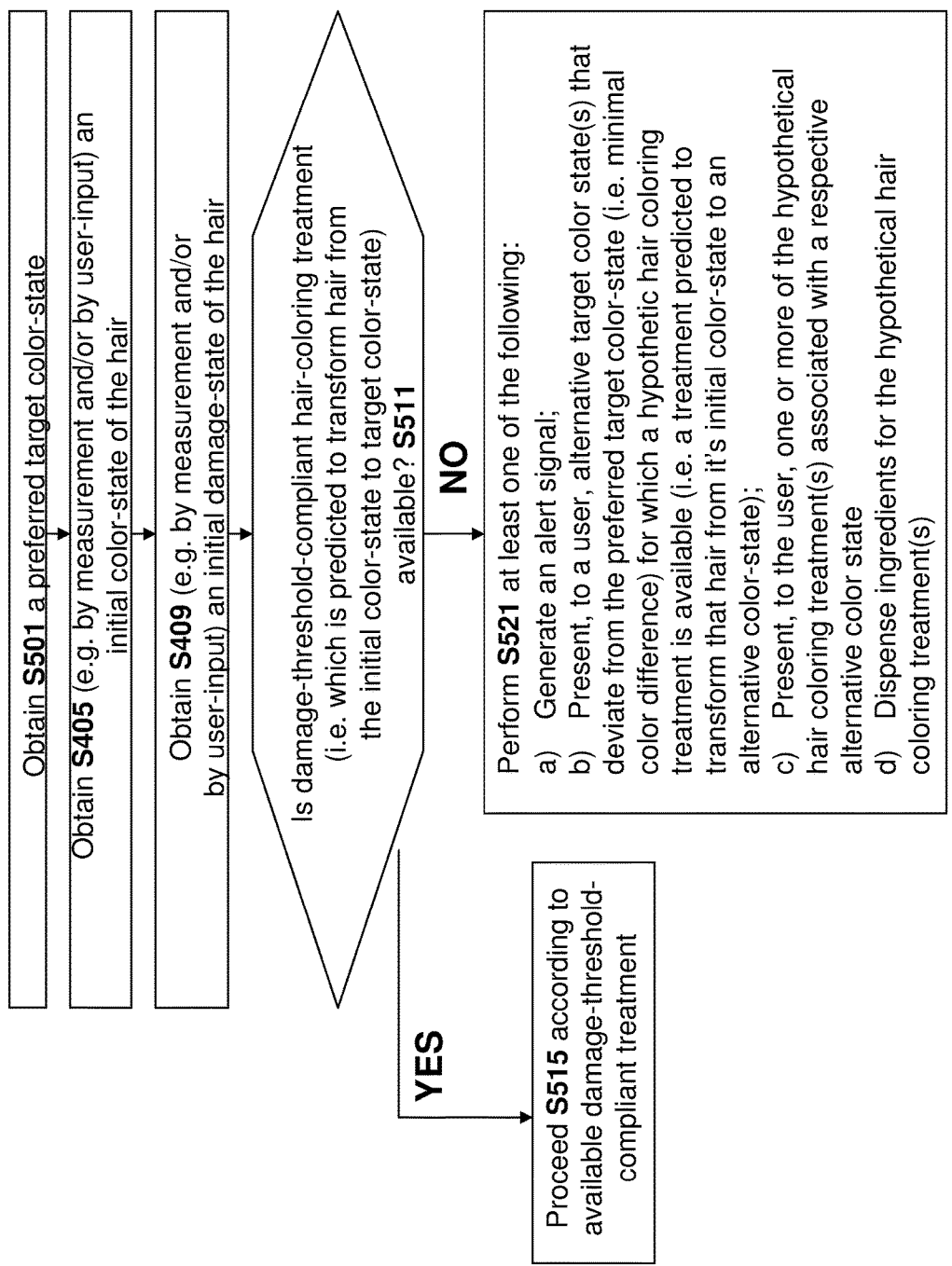

A Discussion of FIG. 11

As noted above, the present inventors are now disclosing that a comparison function and/or disparity function derived from multiple light scattering measurements is a useful tool to quantify hair-damage.

As noted above, hair-damage is cumulative—the greater the initial hair-damage before a hair-coloring treatment, the greater the final hair-damage after the hair-coloring treatment.

Once again, it is possible to create a database and/or look-up table and/or training set for a set of initial hair having different initial damage and a set of hair-coloring treatments. The amount of post-treatment damage (i.e. after hair-coloring treatment) may be computed for the following training set: (i) a number of input types of hair; (ii) different initial-hair damage levels (e.g. as quantified by the disparity function) and (iii) different hair-coloring treatments.

Thus, a tool is provided to predict not only the final color-state of hair, bnut the final damage state-thereof.

It is also possible to define a 'maximum permitted damage threshold' (this threshold may be adjusted in different situations)—for example, according to a disparity function threshold value.

FIG. 11 is a flow chart of a method for hair-coloring. In the example of FIG. 11, the user provides a preferred target color-state in step S501—e.g. a shade of blond. If no hair-coloring treatment that (i) transforms the color-state of the hair from an initial state to a final state and (ii) while doing so, maintains a 'damage state below a permitted maximum threshold, then one or more steps (i.e. any combination) described in step S521 may be performed.

The term 'available' may be defined relative to a pre-defined set of ingredients for a hair-coloring composition—e.g. ingredients present in a dispenser. It may also be defined relative to the pre-defined capabilities of a hair-coloring manufacturing device (e.g. dispenser)—what can be produced.

Thus, in step S511, a determination is made if a damage-threshold-compliant hair-coloring treatment (i.e. which is predicted to transform hair from the initial color-state to target color-state) is available? One or more treatments may, that are predicted to transform hair from the initial color-state to target color-state.

For each of the treatments, a predicted damage state is computed. For example, the predicted damage state as expressed by a predicted value of a disparity function—as mentioned above, such predictions may be made by database or machine-learning or statistical techniques associated with a training set where the pre-treatment and post-treatment is measured.

If such a 'damage compliant' (e.g. without causing the predicted post-treatment hair damage level to exceed a maximum—e.g. without causing the predicted post-treatment disparity function to drop below a minimum) treatment exists, it is possible to proceed in step S515—e.g. by dispensing ingredients from a dispenser device.

Alternatively, if no such treatment exists, one or more (i.e. any combination of) the following steps may be performed: (i) an alert signal may be generated; (ii) the user may be presented with an alternative target color state(s) that is 'similar' to the preferred target color-state presented in step S501 (iii) the user may be presented with a description of a hypothetical hair-color treatment that is predicted to transform the color-state of the hair from its initial state to the alternative target color state in a 'damage compliant manner'; and/or (iv) ingredients required by hypothetical hair-coloring treatment to transform the color-state of the hair from its initial state to the alternative target color state in a 'damage compliant manner'

In one example, related to alternative target color states, the user desired blond hair and this extensive lifting (e.g. by damaging bleach). Because of previous damage to the user's hair, no 'compliant treatment' is available. However, a treatment that renders the hair gold (e.g. by dye rather than by damaging bleach) rather than blond is available. In this case, 'gold' is the computed alternative target color-state. More than one 'alternative target' may be analyzed (i.e. where all are predicted to require only a 'damage-compliant' hair-coloring treatment), and a preferred alternative target in a manner that minimizes a color-difference (e.g. in LAB space) between the alternative target color-state (i.e. which is computed) and the preferred target color-state (i.e. see step S501).

Figure 12A:
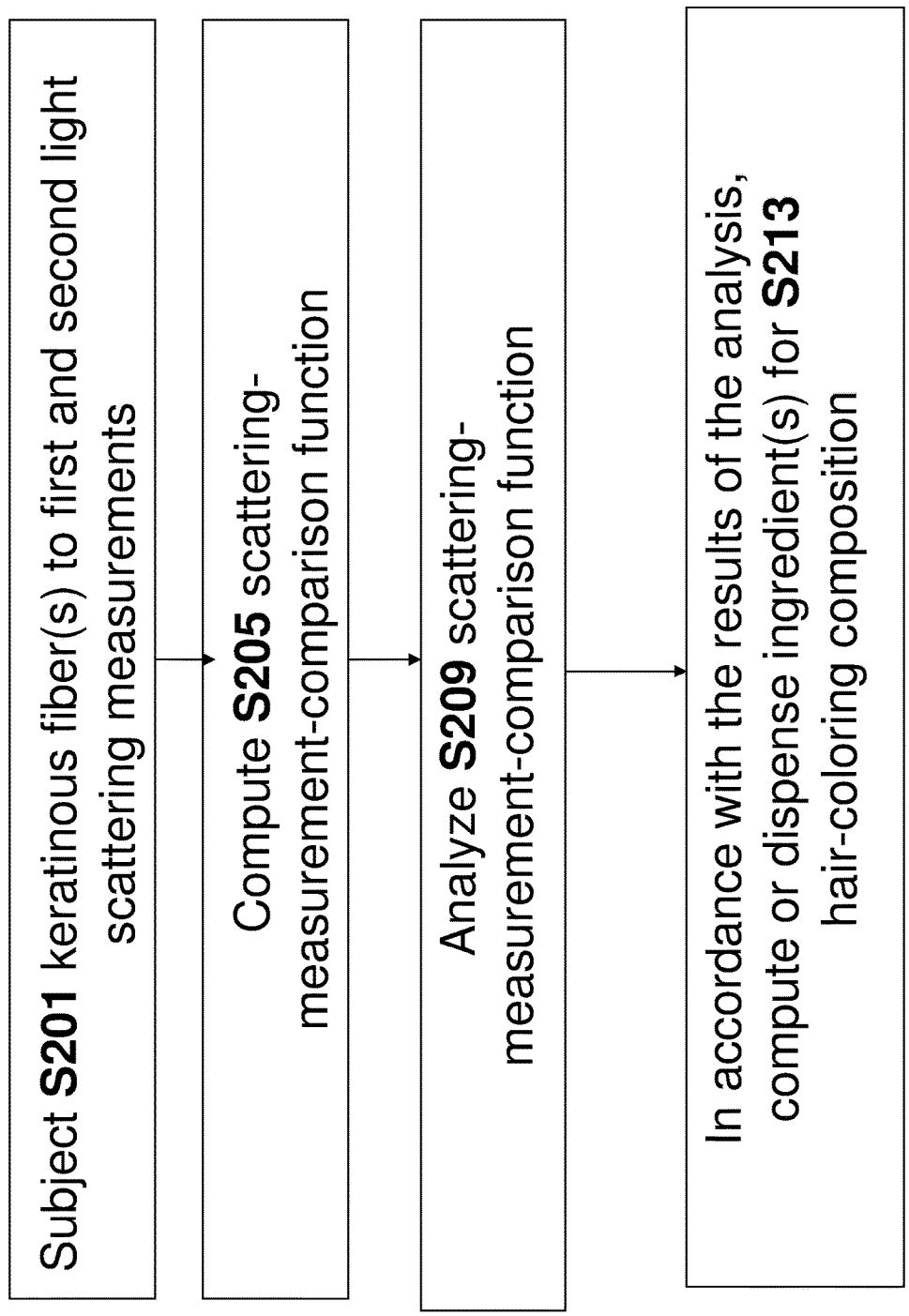
Figure 12B:
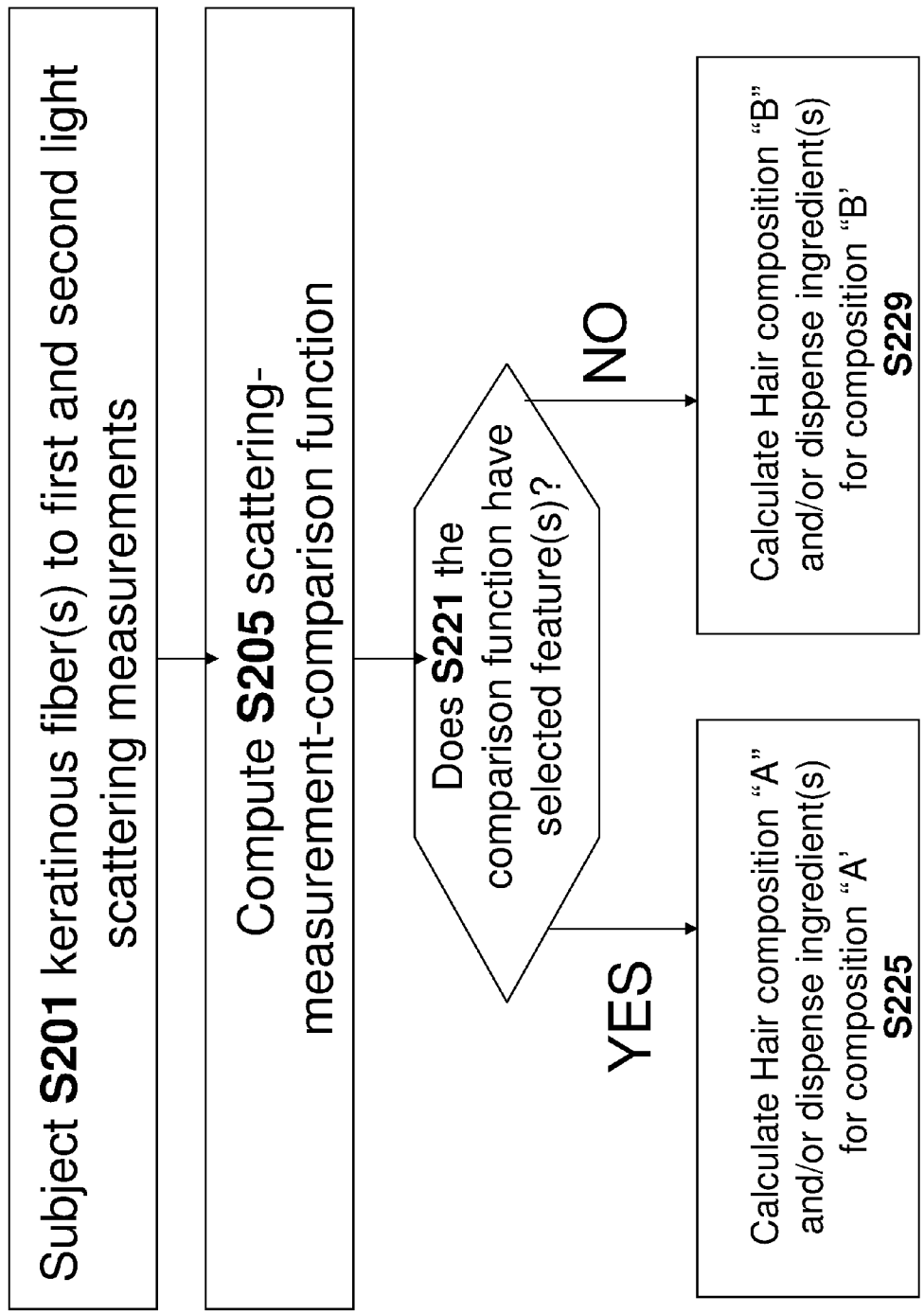
Figure 13:
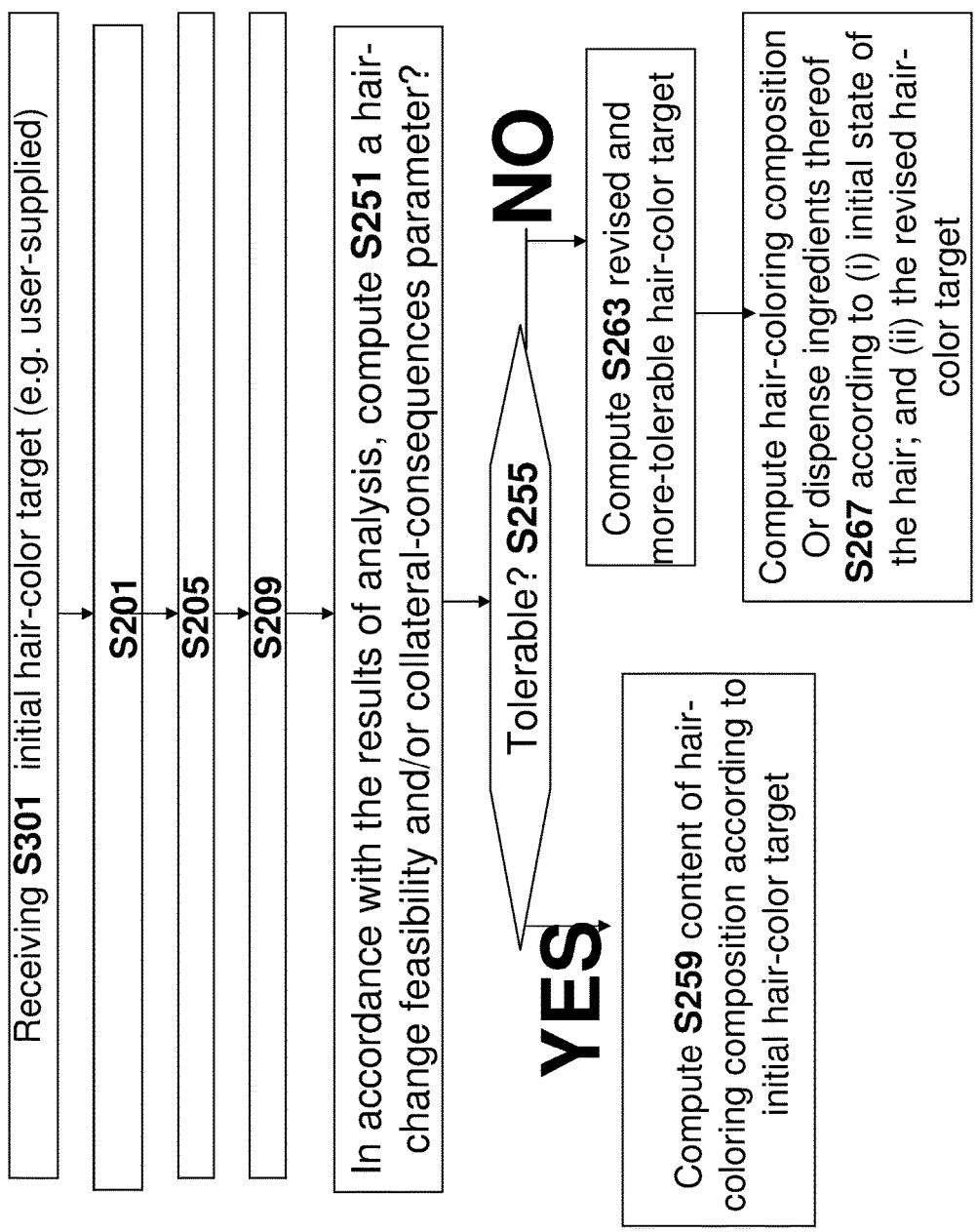
Figure 14:
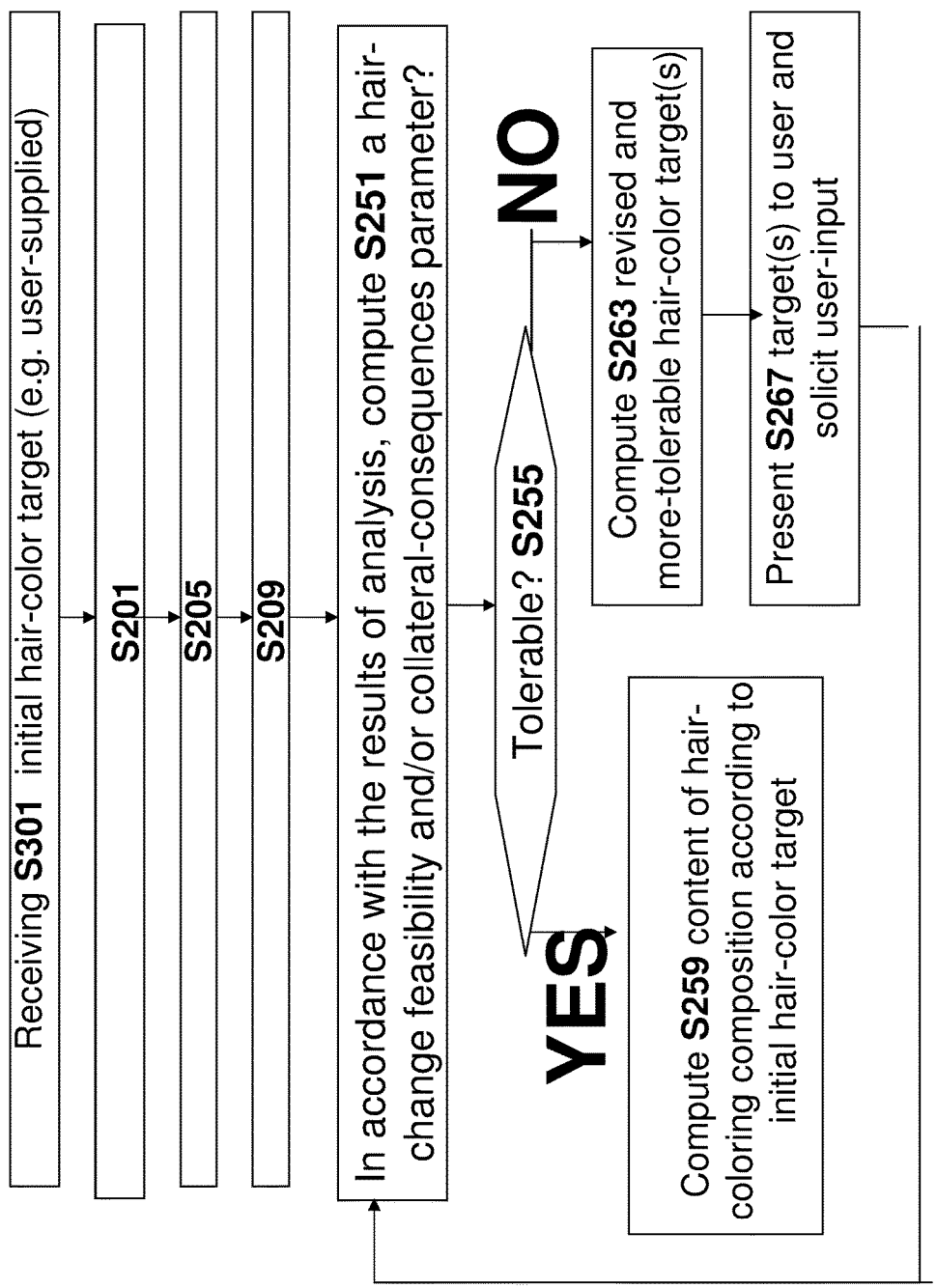

Discussion of FIG. 12-14

Embodiments of the present invention relate to methods and apparatus whereby a content of a hair-coloring composition is computed according to such a scattering-measurement-comparison function. Alternatively or additionally, ingredients of a hair-coloring composition may be computed according to the scattering-measurement-comparison function—e.g. from a dispensing device such as that illustrated in FIG. 10.

For the present disclosure, a 'load' refers to a measurement of quantity—e.g. mass, mole, concentration, volume, or any other measurement FIG. 12A is a flow-chart of a hair-coloring routine. In step S201, keratinous fiber(s) are subjected to first and second light-scattering measurements where for each measurement, a beam of light is incident upon the fibers from a different respective incidence-direction.

In step S205, a scattering measurement-comparison function is computed—e.g. for a single wavelength or over multiple wavelengths (e.g. where the first and second measurements are 'spectra' measurements)—e.g. a ratio such as the (y-value)/(x-value) of FIG. 4. The function is analyzed in step S209.

The results of step S205 and/or of step S209 may be similar to the initial-hair SMCP (scattering measurement comparison function—comparing intensity of scattered light in a pre-determined direction to a collection device(s)).

In step S213, content of a hair-coloring composition is computed and/or ingredient(s) are dispensed (e.g. at quantities or loads matching that of a computed hair-coloring composition) according to the results of the analysis.

One example of the routine of FIG. 12A is illustrated in the flow-chart of FIG. 12B. For example, the 'selected feature' may be a threshold value of an initial-hair SMCP—e.g. at lower values of the SMCP, 'composition A' may be prepared and at higher values of the SMCP 'composition B' may be prepared. For example, 'composition A' may include lower loads of 'ingredient X' while 'composition B' may include higher loads of ingredient X.

In one example, a load of at least one ingredient of the content-computed-hair-coloring composition and/or wherein a load of at least one dispensed ingredient is determined at least in part by the computed scattering-measurement-comparison function.

Examples of 'ingredients' include but are not limited to artificial dyes/colorants, oxidizing agents, and alkylizing agents.

In one non-limiting example (e.g. if a value of the 'comparison function' SCMP is relatively low, the SCMP may be used as a predictor that a given amount of hair-colorant will have a relatively small affect on hair-color, and that a greater quantity may be required to achieve a given dE required to modify the hair color from an initial value to a target value.

Conversely, if a value of the 'comparison function' SCMP is relatively high, the SCMP may be used as a predictor that a given amount of hair-colorant will have a relatively large affect on hair-color, and that only relatively-small quantity is be required to achieve a given dE required to modify the hair color from an initial value to a target value.

The present inventors are disclosing that in situations where a plurality of ingredients are used in a hair-coloring composition, the SMCP function may predict different relative influences of ingredient-load upon hair-color change—i.e. a value of the SMCP may influence required-loads different for different ingredients. As such, the SMCP may be used to predict relative quantities of multiple ingredients that are required or even an average molecular weight.

In some embodiments, a value of an SMCP may indicate that a requested target hair-color may not be appropriate of feasible. For example, it may be computed that a treatment required to achieve the target hair-color inflicts collateral damage upon the hair-strands (step S251-S255). If the amount of collateral damage (or any other collateral 'consequences' parameter) achieves a tolerance threshold (or alternatively, if available hair-treatments are incapable of achieving the hair-color target of step S301, for the user's particular SMCP), it is possible to compute (step S263) an alternative target and, for example, present the alternative target to a user—for example, the alternative target may be similar in Hunter LAB values (or any other color-coordinate) to the initial target but inflict significantly less collateral damage as predicted by the SMCP value.

At that point (e.g. if the user accepts the alternate target hair-color), it may be possible a hair-coloring treatment to achieve the alternative target—e.g. the hair-coloring treatment for achieving this alternative target may also be computed in accordance with the result of step S209.

Figure 15:
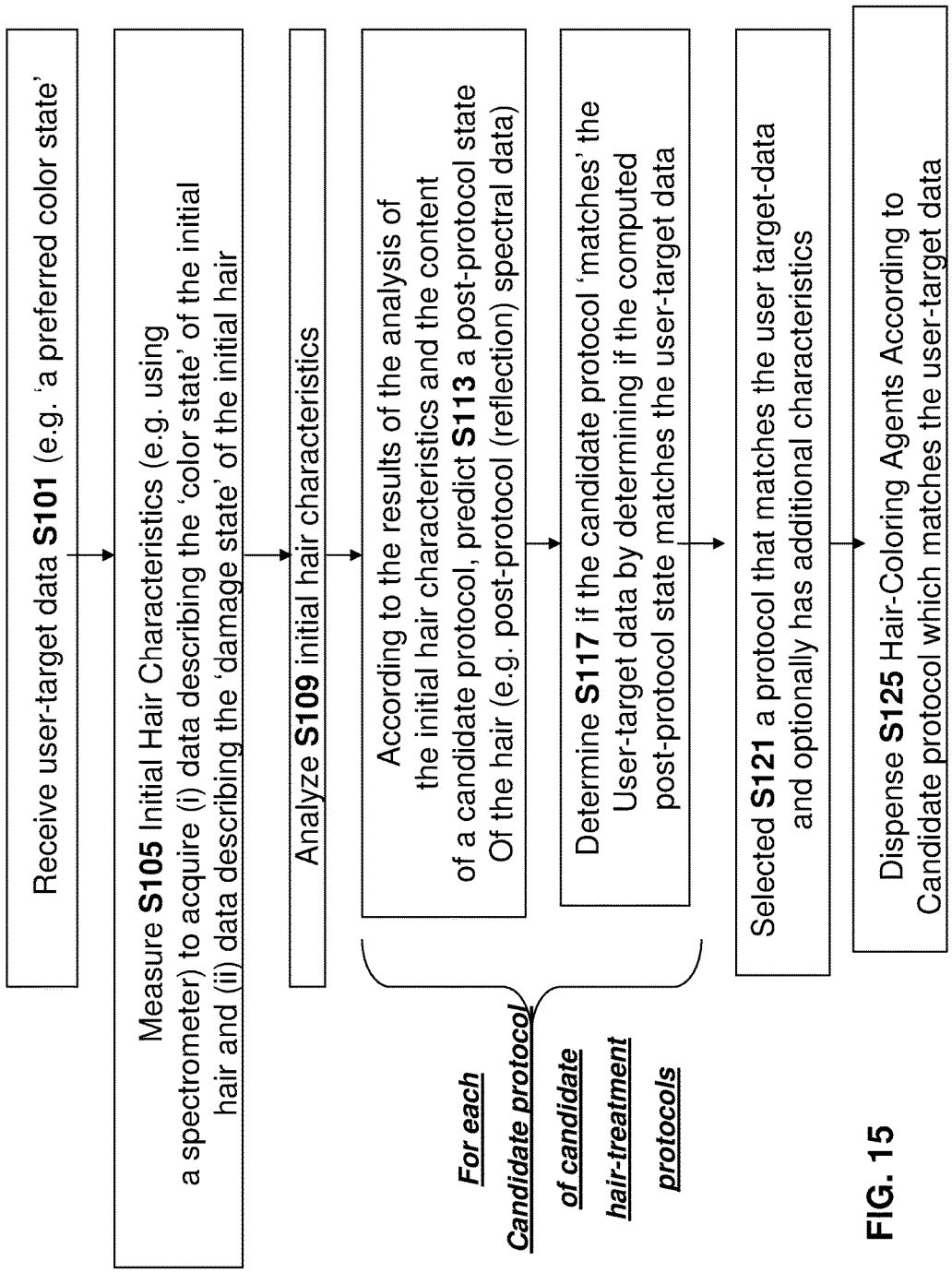

A Discussion of FIG. 15

FIG. 15 is a flow-chart of an exemplary technique for hair-coloring. In step S101, user-target data is received and stored (e.g. in volatile and/or non-volatile computer-readable storage). Typically, the user-target data relates to a selected shade or color—e.g. a user desires to color his/her hair to the selected shade or color. In step S105, characteristic of a user's hair are measured—e.g. using at least a spectroscopic hair-reader device such as that illustrated in FIG. 2 or 4, discussed below. These characteristics may be electronically analyzed in step S109. According to the technique of FIG. 1, it is possible to compute a 'customized' hair-treatment that is specific to (i) an initial pre-treatment state of the user's hair (e.g. as measured in step S105 and analyzed in step S109) and (ii) the user-target data.

The term 'user-target' typically includes to a target color shade—e.g. expressible as a value in color-space such as Hunter Lab color space or any other color space. In addition to a target color shade, user-target data may also include some other desired characteristic of any proposed hair-treatment—e.g. a treatment of 'roots-only' as opposed to 'entire-hair-shaft,' a maximum treatment time, etc.

A plurality of hypothetical or 'candidate' hair-treatment protocols may be analyzed and considered. A 'hair-treatment' typically refers to at least absolute or relative quantities or 'loads' (i.e. expressed in molar terms, or as weights, or a volumes, or in any other manner known in the art) of one or more hair-coloring agents. The term 'hair-coloring agent' may include an artificial colorant/dye, an oxidizer, an alkalizer or an other substance used in the art for temporary, semi-permanent, demi-permanent or permanent hair-coloring. A hair-coloring agent may be in any phase or form, including but not limited to liquid, gel, mouse, cream, solid, powder, tablet, or any other form known in the art. Optionally, a 'hair-treatment' also includes data relating to treatment time, treatment temperature, multi-stage treatments or any other parameter of treatment. For example, a hair-treatment may entail production of multiple distinct combinations of hair-coloring agents—e.g. a coloring mixture and a bleaching mixture which are applied in different stages.

Typically, the specific characteristics of each user's hair is quite individual (e.g. based upon his/her genotype, age, environmental effects etc.) and the number of potential target shades or colors may also be relatively large. Because of the myriad possible combinations of initial and target hair characteristics, the number of possible candidate/hypothetical hair-treatment protocols may be extremely large, and it is not always known a priori which hair-treatment protocols are predicted to be effective (or most effective) to transform hair from its initial state to a state matching the target data received in step S101.

As such, it may be necessary to electronically analyze multiple hypothetical hair treatments to identify a treatment (or set of more than one hypothetical hair-treatments) which successfully transforms the initial hair to a target color.

This is done in steps S113 and S117. Thus, in step S113, a post-protocol state for the hair is predicted for the hair-characteristics measured in step 105 and a specific candidate hair-treatment. In step S117, it is electronically determined if this post-protocol state matches the specifications of the user target-data.

The term 'hair-color treatment' is not restricted to introducing colorants (e.g. artificial colorants) into the hair (i.e. 'coloring') but may also include hair-bleaching.

In one non-limiting example, (i) in step 105 one or more initial reflection spectum(a) are measured, (ii) in step S113 a hypothetical post-treatment reflection spectrum is computed from the initial reflection spectrum and specifics of a candidate hair-treatment protocol, and a color value (e.g. an LAB value) is computed from the hypothetical post-treatment reflection spectrum; and (iii) in step S117 this initial-hair-specific and candidate-protocol-specific LAB value is compared to an LAB value associated with the user-target data received in step S101.

In step S121, a protocol that matches the user target-data is selected. Optionally, for example, if more than one candidate protocol matches the user target-data, these candidate protocols may be analyzed and/or scored, and a more preferred matching hair-coloring protocol may be selected accordingly.

In step S125, according to the selected hair-coloring protocol, respective quantities of hair-coloring agent, for a plurality of hair-coloring agents, are each dispensed according to a specifics of the hair-coloring protocol selected in step S121. One non-limiting example of a dispenser of hair-coloring agents is illustrated in FIG. 3. In this non-limiting example, different respective hair-coloring agents are disposed in each container of a plurality of containers 180A-180Q. In response to the results of step S121, for at least 2 or at least 3 or at least 4 or at least 5 or at least any number of hair-coloring agents, respective quantities of each hair-coloring agent are dispensed into a vessel (not shown) located in port 192.

In some embodiments, the dispenser is automatic and includes electronic circuitry for regulating quantities of hair-coloring agents that are dispensed.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one. (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons skilled in the art.

What is claimed:

1. A hair coloring method comprising:
   a. performing a plurality of light-scattering measurements upon a sample of hair such that for each light-scattering measurement, the sample of hair is illuminated from a different respective direction;
   b. comparing the results of the light-scattering measurements by computing a ratio between respective intensities of light scattered by the hair during each of the scattering measurements;
   c. in accordance with results of the comparing, computing an initial damage-state of hair of the sample by comparing the results of the light-scattering measurements;
   d. obtaining an initial color-state of the hair of the sample; and
   e. computing a hair-coloring composition that is predicted to transform the hair sample from the initial color-state to a target color-state such that in response to a determining of a greater or lesser extent of initial damage, a concentration of artificial-colorant(s) within the computed coloring composition is reduced or increased respectively.

2. The method of claim 1 wherein:
i. the hair-coloring composition comprises first and second artificial-colorants;
ii. the rate of absorbance by hair-shafts of the first artificial-colorant exhibits a greater dependency upon an extent of damage to the hair-shafts than the rate of absorbance of hair-shafts of the second artificial-colorant; and
iii. in response to a determining of a greater extent of initial damage, a ratio between respective concentrations of the first and second artificial-colorants within the hair-coloring composition decreases.

3. A method of coloring hair according to (i) a preferred target color-state and (ii) a maximum hair-damage-threshold, the method comprising:
a. obtaining descriptions of an initial damage state of the hair and an initial color-state of the hair; and
b. according to the initial damage-state of the hair, determining an availability of a damage-threshold-compliant hair-coloring treatment that is predicted to (i) successfully transform the color-state of the hair from the initial color-state to the preferred target color-state; and (ii) is predicted to maintain a damage-state of the hair below the maximum-damage-threshold; and
c. in response to a determination that the damage-threshold-compliant hair-treatment is not available, performing at least one of the following: (i) presenting to a user one or more alternate target color-states where each alternate target color-state: A. deviates from the preferred target color-state; and B. is associated with a damage-threshold-compliant hypothetical hair-treatment that is predicted to transform the color-state of the hair from the initial color-state to the alternate target color-state: I. without exceeding the damage-threshold; and II. in a manner that minimizes a color-difference between the alternate color-state and the preferred target color-state; (ii) presenting to a user a description of one or more of the damage-threshold-compliant hypothetical treatments; (iii) dispensing ingredients for a hair-coloring composition required by the damage-threshold-compliant hypothetical treatment; and (iv) generating an alert signal,
wherein the obtaining of the description of the initial damage state of the hair comprises:
i. performing a plurality of light-scattering measurements upon a sample of hair such that for each light-scattering measurement, the sample of hair is illuminated from a different respective direction; and
ii. comparing the results of the light-scattering measurements.

4. A method of measuring a hair damage-state, the method comprising:
a. subjecting a hair-shaft-aligned sample of hair to first and second light-scattering measurements such that: (i) the hair-shafts of the sample of hair are aligned with each other so as to collectively define a hair-alignment axis; (ii) for each light-scattering measurement, the hair is illuminated from a different respective hair-illumination direction; (iii) the hair-illumination directions and the hair-alignment directions are all co-planar;
b. electronically comparing the results of the light-scattering measurements by computing a ratio between respective intensities of light scattered by the hair during each of the scattering measurements; and
c. in accordance with the results of the comparing, computing a damage-state of hair of the sample.

5. The method of any of claims 1 and 4, wherein light-scattering measurements are performed so that the collection direction(s) for each of the light-scattering measurements are the same.

6. The method of any of claims 1 and 4, wherein the light-scattering measurements are performed upon a sample of aligned hair-shafted that are aligned to define a hair-shaft alignment axis.

7. The method of claim 6 wherein collection direction(s) for each light-scattering measurement are in a plane that is perpendicular to the hair-shaft alignment axis.

8. The method of any of claims 1 and 4, wherein the light-scattering measurements are performed so that scattered light for each light-scattering measurement is collected by the same collection device.

9. The method of any of claims 1 and 4 wherein the initial color-state is optically measured by an instrument including photodetector(s).

10. The method of any of claims 1 and 4 wherein the initial color-state comprises at least one of spectral data, and a color-space value (e.g. LAB value or RGB value).

11. The method of any of claims 1 and 4 wherein shafts of the hair-sample are aligned along an alignment axis.

12. The method of claim 11 wherein each of the beam-incidence-directions is substantially 0-degree-azimuth or substantially 180-degree-azimuth relative to the alignment axis and an azimuth-plane.

13. The method of claim 12 wherein the azimuth plane is perpendicular a perpendicular plane defined by the alignment axis and a hair-detector light-scattering direction for at least one of the light-scattering measurements.

14. The method of claim 13 wherein the azimuth plane is perpendicular to a perpendicular plane defined by the alignment axis and a hair-detector light-scattering direction for all of the light-scattering measurements.

15. The method of claim 1 wherein:
i. the light-scattering measurements are performed by a hair-reading device having a device-housing including a planar housing-window;
ii. for each of the light-scattering measurements, source-light exits out of the device-housing via the planar housing-window to illuminate the hair and scattered-light from the hair enters into the device-housing via the planar housing-window; and
iii. the azimuth plane is defined as the plane of the housing-window.

16. The method of claim 1, wherein the first and second incidence directions subtend at least 10 degrees or at least 15 degrees or at least 20 degrees and/or at most 80 degrees or at most 70 degrees.

17. The method of claim 1, wherein an elevation-angle difference between the first and second incidence directions, as defined by the azimuth-plane, is at least 10 degrees or at least 15 degrees or at least 20 degrees and/or at most 80 degrees or at most 70 degrees.

18. The method of claim 1, wherein for each of the first and second reflection measurements, a detection-direction of light reflected by the aligned keratinous fiber(s) is substantially the same.

19. The method of claim 1, wherein a common photodetector respectively detects scattered light for each scattering measurement so as to generate each scattered-light-indicative electrical signal.

20. The method of claim 1, further comprising: in response to the computing of the hair-coloring composition, automatically dispensing ingredients to achieve the adjusted concentration of artificial-colorant(s).

21. A system for performing operations related to hair-coloring, the system comprising:
   a. a hair-reader device configured to perform a plurality of light-scattering measurements upon a sample of hair such that for each light-scattering measurement, the sample of hair is illuminated from a different respective direction;
   b. electronic circuitry, configured to:
      i. compare the results of the light-scattering measurements by computing a ratio between respective intensities of light scattered by the hair during each of the scattering measurements;
      ii. in accordance with results of the comparing, compute an initial damage-state of hair of the sample by comparing the results of the light-scattering measurements; and
      iii. compute a hair-coloring composition that is predicted to transform the hair sample from an initial color-state to a target color-state such that in response to a determining of a greater (lesser) extent of initial damage, a concentration of artificial-colorant(s) within the computed coloring composition is reduced (increased).

22. The system of claim 21 wherein:
   i. the hair-coloring composition comprises first and second artificial-colorants;
   ii. the rate of absorbance by hair-shafts of the first artificial-colorant exhibits a greater dependency upon an extent of damage to the hair-shafts than the rate of absorbance of hair-shafts of the second artificial-colorant; and
   iii. in response to a determining of a greater extent of initial damage, a ratio between respective concentrations of the first and second artificial-colorants within the hair-coloring composition decreases.

23. The system of claim 21, further comprising a dispenser device configured, in response to the computing of the hair-coloring composition, to automatically dispense ingredients to achieve the adjusted concentration of artificial-colorant(s).

* * * * *

UNITED STATES PATENT AND TRADEMARK OFFICE
CERTIFICATE OF CORRECTION

Page 1 of 1

PATENT NO.         : 10,012,588 B2
APPLICATION NO.    : 15/303726
DATED              : July 3, 2018
INVENTOR(S)        : Efraim Miklatzky et al.

It is certified that error appears in the above-identified patent and that said Letters Patent is hereby corrected as shown below:

On the Title Page

Item (72) Inventors, second inventor, Elena Ishkov, Givataim (IL), please change "Givataim" to --Givatayim--; and In the Claims Column 22, Line 31, Claim 13 after the word "perpendicular", add the word --to--.

Signed and Sealed this
Eighteenth Day of June, 2019

Andrei Iancu
*Director of the United States Patent and Trademark Office*